United States Patent [19]

Haugwitz et al.

[11] Patent Number: 5,681,832

[45] Date of Patent: Oct. 28, 1997

[54] AROYLANILINE COMPOUNDS, PHARMACEUTICAL COMPOSITIONS, AND METHODS OF USING SAME TO INHIBIT VIRAL ACTIVITY

[75] Inventors: Rudiger D. Haugwitz, Bethesda, Md.; Leon Zalkow; Ewa Gruszecka-Kowalik, both of Atlanta, Ga.; Edward Burgess, Marietta, Ga.

[73] Assignees: The United States of America as represented by the Department of Health and Human Services, Washington, D.C.; Georgia Tech Research Corporation, Atlanta, Ga.

[21] Appl. No.: 390,057

[22] Filed: Feb. 17, 1995

[51] Int. Cl.$^6$ .................. A61K 31/655; C07D 215/16; C07D 215/20
[52] U.S. Cl. .................. 514/150; 514/312; 514/314; 534/759; 534/820; 546/156
[58] Field of Search ................... 534/759, 820; 546/156; 562/47, 48, 49, 50; 514/150, 314, 312

[56] References Cited

U.S. PATENT DOCUMENTS

| | | | |
|---|---|---|---|
| 2,448,853 | 8/1948 | Allen et al. | 534/820 X |
| 3,211,554 | 10/1965 | Dreyfuss | 534/820 X |
| 3,562,248 | 2/1971 | Jones et al. | 534/820 X |
| 4,118,232 | 10/1978 | Piller et al. | 534/820 X |
| 4,167,509 | 9/1979 | Parton | 534/759 X |
| 4,542,139 | 9/1985 | Hitzel et al. | 546/156 X |
| 4,621,088 | 11/1986 | Larselle et al. | 546/156 X |
| 5,043,257 | 8/1991 | Baettig et al. | 430/563 |

FOREIGN PATENT DOCUMENTS

| | | | |
|---|---|---|---|
| 2166146 | 4/1986 | United Kingdom | 534/820 |
| 93 16992 | 9/1993 | WIPO. | |
| 94 14763 | 7/1994 | WIPO. | |

OTHER PUBLICATIONS

Hurst et al., "The Prevention of Encephalitis Due to the Viruses of Eastern Equine Encephalomyelitis and Louping-Ill: Experiments with Trypan Red . . . ", *Brit J. Pharmacol.*, 7, 455 (1952).

Balzarini et al., "Comparative Inhibitory Effects of Suramin and Other Selected Compounds on the Infectivity and Replication of Human T-Cell Lymphotropic Virus . . . ", *Int. J. Cancer*, 37, 451–457 (1986).

*The Merck Index*, eleventh edition, 1423 (1989.

Kaplan et al., "Lack of Response to Suramin in Patients with AIDS and AIDS–Related Complex", *The American Journal of Medicine*, 82, 615–620 (1987).

Erik De Clercq, II "Suramin in the treatment of AIDS: mechanism of action", *Antiviral Research*, 7, 1–10 (1987).

Alarcon et al., "Screening for new compounds with antiherpes activity", *Antiviral Research*, 4, 231–243 (1984).

Thorne et al., "Inactivation of Measles and Herpes Simplex Viruses by Trypan Blue", *Journal Gen. Virol*, 64, 1365–1368 (1983).

Akerfeldt et al., "Aromatic Sulfonic Acids as Vital Inhibitors. Structure–Activity Study using Rhino, Adeno 3, Herpes Simplex, and Influenza Viruses", *Journal of Med. Chem.*, 14, 596–600 (1971).

Mohan et al. I, "Potential Anit–AIDS Agents. Synthesis and Antiviral Activity of Naphthalenesulfonic Acid Derivatives against HIV–1 and HIV–2", *Journal Med. Chem.*, 34, 212–217 (1991).

Schols et al., "Flow Cytometric Method to Demonstrate Whether Anti–HIV–1 Agents Inhibit Virion Binding to T4+ Cells", *Journal of Acquired Immune Deficiency Syndrome* 2, 10–15 (1989).

De Clercq, I "Suramin: A Potent Inhibitor of the Reverse Transcriptase of RNA Tumor Viruses", *Cancer Letters*, 8, 9–22 (1979).

Broder et al., "Effects of Suramin on HTLV–III/LAV Infection Presenting As Kaposi's Sarcoma or Aids–Related Complex: Clinical Pharmacology and Suppression of . . . ", *The Lancet*, 2, 627–630 (1985).

Mohan et al. II, "Potential Anti–AIDS Agents. Synthesis and Antiviral Activity of Naphthalenesulfonic Acid Derivatives against HIV–1 and HIV–2", *J Med. Chem.*, 34, 212–217 (1991).

Tan et al., "Potential Anti–AIDS Naphthalenesulfonic Acid Derivatives. Synthesis and Inhibition of HIV–1 Induced Cytopathogenesis and HIV–1 and HIV–2 Reverse . . . ", *J. Med. Chem.*, 35, 4846–4853 (1992).

Mohan et al. III, "Structure–Activity Relationship Studies with Symmetric Naphthalenesulfonic Acid Derivatives. Synthesis and Influence of Spacer and . . . ", *J. Med. Chem.*, 36, 1996–2003 (1993).

Gulakowski et al, J. Virological Methods, vol. 33, pp. 87–100 (1991).

Hein et al., "Optical Bleaching Agents. I. Derivatives of Dichloroaminostilbenedisulfonic Acid", *Journal Of American Chemical Society*, 76, 2725–2731 (1954).

Aleksandrov et al., "Diacyl and diacyldisulfamide derivatives of 4,4'–diaminostilbene–2,2'–disulfonic acid", *Chemical Abstracts*, 85, 359–360 (1976).

Ohyama et al., "Silver halide emulsion", *Chemical Abstracts*, 52, 8810–8811 (1958).

Database Crossfire, Beilstein Informationssysteme GmbH, Frankfurt DE, XP002005441, see BRN=2928122 & *Chemical Abstracts*, vol. 72, No. 24, 1970, Columbus, Ohio, US; abstract No. 122893.

Database Crossfire, Beilstein Informationssysteme GmbH, Frankfurt DE, XP002005442, see BRT–2193992 & *Kogyo Kagaku Zasshi*, vol. 74, No. 1971, pp. 729–732.

Database Crossfire, Beilstein Informationssysteme GmbH, Frankfurt DE, XP002005443, see BRN=2795085 & *Yuki Gosei Kagaku Kyokaishi*, vol. 30, 1972, pp. 818–819.

(List continued on next page.)

*Primary Examiner*—Floyd D. Higel
*Attorney, Agent, or Firm*—Leydig, Voit & Mayer, Ltd.

[57] ABSTRACT

Aroylaniline compounds which exhibit anti-retroviral activity, pharmaceutical compositions containing such aroylaniline compounds, and methods for treating a retroviral-infected host comprising administering an antiviral effective amount of an aroylaniline compound to a host.

31 Claims, 3 Drawing Sheets

OTHER PUBLICATIONS

Database Crossfire, Beilstein Informationssysteme GmbH, Frankfurt DE, XP002005444, see BRT=2785594 &*Justus Liebigs Ann. Chem*, vol. 692, 1966, pp. 26–41.

Database Crossfire, Beilstein Informationssysteme GmbH, Frankfurt DE, XP002005445, see BRT–2928923 & *Chemical Abstracts*, vol. 72, No. 24, 1970, Columbus, Ohio, US; abstract No. 122893.

Database Crossfire, Beilstein Informationssysteme GmbH, Frankfurt DE, XP002005446, see BRN=2826422 & *Chemical Abstracts*, vol. 53, No. 21, 10 Nov. 1959, Columbus, Ohio, US; abstract No. 19944b.

Database Crossfire, Beilstein Informationssysteme GmbH, Frankfurt DE, XP002005447, see BRN=2797601 & *Chemical Abstracts*, vol. 72, No. 24, 1970, Columbus, Ohio, US; abstract No. 122893.

Database Crossfire, Beilstein Informationssysteme GmbH, Frankfurt DE, XP002005448, see BRN=2928566 &*Chemical Abstracts*, vol. 72, No. 24, 1970, Columbus, Ohio, US; abstract No. 122893.

Database Crossfire, Beilstein lnformationssysteme, GmbH, Frankfurt DE, XP002005449, see BRN=3192102 & DE, C, 250 342 (Bayer & Co.) 1914.

Database Crossfire, Beilstein Informationssysteme GmbH, Frankfurt DE, XP002005450, see BRN=2930702 & *J. Soc. Dyers Colour.*, pp. 102–104.

Database Crossfire, Beilstein Informationssysteme GmbH, Frankfurt DE, XP002005451, see BRN=4050045 & *Biochemistry*, vol. 18, 1979 pp. 4505–4510.

Database Crossfire, Beilstein Informationssysteme GmbH, Frankfurt DE, XP002005452, see BRN=2932158 & *Yuki Gosei Kagaku Kyokaishi*, vol. 29, 1971, pp. 519–522.

AROYLANILINE COMPOUNDS, PHARMACEUTICAL COMPOSITIONS, AND METHODS OF USING SAME TO INHIBIT VIRAL ACTIVITY

TECHNICAL FIELD OF THE INVENTION

The present invention is directed, in general, to aroylaniline compounds which exhibit antiviral activity, methods for synthesizing these aroylaniline compounds, pharmaceutical formulations containing these compounds, and methods for treating viral infections, particularly those caused by a human immunodeficiency virus, such as HIV.

More particularly, the present invention is related to substantially pure aroylaniline derivatives and related compounds wherein the central double bond is replaced with, for example, a methylene-, ethylene-, hetero atom-, amido-, ureido- or thioureido-linkage, as well as pharmacological uses and compositions thereof.

BACKGROUND OF THE INVENTION

Only a decade ago, acquired immune deficiency syndrome (AIDS) was virtually unknown. This puzzling affliction was seen only in a small number of homosexual men. However, today it is difficult to find anyone who has not heard of AIDS, the disease that can debilitate and then kill its victim.

AIDS is a fatal disease, reported cases of which have increased dramatically within the past several years. Estimates of reported cases also continue to rise dramatically. Consequently, there is a great need to develop drugs and vaccines to combat AIDS.

The virus which is the causative agent of AIDS was first identified in 1983. Since 1983 the AIDS-causing virus has been known by several names and acronyms. Most recently, it has been referred to as human immunodeficiency virus (HIV). It has also been known as lymphadenopathy-associated virus (LAV) and AIDS-related virus (ARV). HIV is the third known T-lymphocyte virus (HTLV-III), and it has the capacity to replicate within cells of the immune system, causing profound cell destruction. The AIDS virus is a retrovirus, which is a virus that uses reverse transcriptase during replication. Two distinct families of HIV have been described to date, namely HIV-1 and HIV-2. The acronym HIV will be used herein to refer to HIV viruses generically. Thus far, there is no cure for AIDS.

Specifically, HIV is known to exert a profound cytopathic effect on the CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. There are many ways in which an agent can exhibit anti-retroviral activity. For example, HIV requires at least four viral proteins for replication: reverse transcriptase (RT), protease (PR), transactivator protein (TAT), and regulator of virion-protein expression (REV). Accordingly, viral replication could theoretically be inhibited through inhibition of any one or all of the proteins involved in viral replication. Anti-retroviral agents, such as AZT and ddC, are known to inhibit RT. There also exist anti-retroviral agents that inhibit TAT.

Nucleoside derivatives, such as AZT, are the only clinically active agents that are currently available for antiviral therapy. Although very useful, the utility of AZT and related compounds is limited by toxicity and insufficient therapeutic indices for fully adequate therapy. The development of AZT-resistant strains of HIV also limits the utility of AZT in the treatment of AIDS.

Synthetic peptides also are being developed for potential use as inhibitors of the retroviral PR in the treatment of AIDS. Although these inhibitors are effective in preventing the retroviral PR from functioning, the inhibitors suffer from some distinct disadvantages. First, since the active site of the PR is hindered, i.e., has reduced accessibility as compared to the remainder of the PR, the ability of the inhibitors to access and bind in the active site of the PR is impaired. Secondly, the peptide inhibitors that bind to the active site of the PR are generally poorly soluble in water, causing distinct problems in drug delivery.

Dyes, particularly azo dyes, have also been discovered to exhibit antiviral activity. For example, compounds which exhibit potential antiherpes activity include the azo dye Trypan Blue (Alarcon et al., "Screening for New Compounds with Antiherpes Activity," *Antiviral Res.*, 4 231–243 (1984); and Thorne et al., "Inactivation of Measles and Herpes Simplex Viruses by Trypan Blue," *J. Gen. Virol.*, 64, 1365–1368 (1983)), as well as Indigocarmine and Paraorange (Westin et al., "Aromatic Sulfonic Acids as Inhibitors: Structure-Activity Study Using Rhino, Adeno 3, Herpes Simplex, and Influenza Viruses," *J Med. Chem.*, 14, (7), 596–600 (1971)). The azo dye Congo Red and derivatives thereof have also been investigated for potential anti-AIDS activity (Mohan et al., "Potential Anti-AIDS Agents. Synthesis and Anti-viral Activity of Naphthalenesulfonic Acid Derivatives Against HIV-1 and HIV-2," *J. Med. Chem.*, 34, 212–217 (1991)), and the azo dye Evans Blue (Schols et al., "Flow Cytometric Method to Demonstrate Whether Anti-HIV-1 Agent Inhibit Virion Binding to T4+ Cells," *J. of Acquired Immune Deficiency Syndromes*, 2, 10–15 (1989)). Further, a number of azo dyes were demonstrated to exhibit protective properties in mice infected by equine encephalomyelitis virus (Hurst et al., *Brit. J. Pharmacol.*, 7, 455 (1952)). Eric De Clercq in Anticancer Research, 7, 1023 (1987), and in the *Int. J. Cancer*, 37, 451 (1986), summarized the perspectives for the chemotherapy of AIDS. These reviews mention two polyanionic dyes with proven anti-HIV activity, i.e., Evans Blue, an azo dye, which is available in 85% purity (Aldrich 1994) and aurintricarboxylic acid which has recently been shown to be a polymeric mixture, and not a monomeric substance. Other anti-virally active azo dyes are disclosed in U.S. application Ser. No. 08/167,296. Thus, dye compounds have been shown to exhibit antiviral activity.

While the above azo dyes have demonstrated anti-HIV activity, they tend to dye the tissues of man or domestic animals. These staining properties have obvious disadvantages. However, the compounds of the present invention were developed based on the discovery that the virucidal activity of such compounds was due to the binding on the uninfected cells, thus preventing attachment/fusion of the virus. Therefore, compounds with similar affinities but lacking the chromophoric azo linkages may express similar biological activity without the disadvantages associated with staining tissue. For example, suramin, an effective agent for the treatment of early cases of human African trypanosomiasis (*Burger's Medicinal Chemistry, fourth edition, part II*, 444) was developed by replacement of an azo linkage with an amido linkage. Suramin, hexasodium sym-bis(m-aminobenzoyl-m-amino-p-methylbenzoyl-1-naphthyamino-4,6,8-trisulfonate)carbamide, has no azo linkages. The color of suramin is off white (*The Merck Index*, eleventh edition, 1423). In spite of suramin's disappointing performance in AIDS patients (L. D. Kaplan et al., "Lack of response to suramin in patients with AIDS and AIDS-related complex", *Amer. J. Med.*, 82, 615–20 (1987)), suramin has been investigated in detail (DeClercq, E., "Suramin: A potent inhibitor of the reverse transcriptase of RNA tumor viruses", *Cancer Lett.*, 8:9–22 (1979); Broder, S., Yarchoan R., Collins, J. M. et al., "Effects of suramin on HTLV-III/LAV infection presenting as Kaposi's sarcoma or AIDS-related complex: Clinical pharmacology and suppression of viral replication in vivo", *Lancet*, 2:627–30 (1985); Balzarini, J. Mitsuya H., DeClercq, E., Broder, S., "Comparative inhibitory effects of suramin and other selected compounds on the infectivity and replication of human T-cell lymphotropic virus (HTLV-III)/lymphadenopathy-associated virus (LAV) ", *Int. J. Cancer*, 37:451–7 (1986); DeClercq, Suramin in the Treatment of AIDS "Mechanism of Action", *Antiviral Res.*, 7, 1–10 (1987); and Nickel, P. et al., "Potentielle Filarizide, Arzneimittel Forschung", 36 (II) #8, 1153–57 (1986). Mohan et al. have extensively investigated compounds related to suramin. These compounds share the terminal naphthalenesulfonic acid moieties but the substitution pattern of the naphthalenes is different. (Mohan, P. et al., "Naphthalenesulfonic acid derivatives. Potential Anti-AIDS agents", *J. Med. Chem*, 34(#1), 212–217 (1991); 35(#26), 4846–4853 (1992), 36(#34), 1996–2003 (1993)).

In addition to the tissue staining properties of azo dyes, such compounds may form metal chelates and are thus difficult to formulate.

In view of the above it is desirable to obtain compounds which exhibit biological activity such as virucidal activity with reduced or no staining properties and which are soluble and easier to formulate.

In view of the above, there is a need for compounds which exhibit biological activity such as virucidal activity with reduced or no staining properties which may be used alone or in combination with AZT and/or other agents in the treatment of viral infections, particularly AIDS. The present invention seeks to provide such compounds as well as related compositions and methods of using such compositions. These and other objects of the present invention, as well as additional inventive features, will be apparent from the description of the invention provided herein.

BRIEF SUMMARY OF THE INVENTION

In accordance with the present invention, it has now been discovered that certain compounds, specifically, aroylaniline compounds as defined in Formula I below, are capable of preventing the replication of a virus in a cell, such as a human T-cell, infected with such a virus, without staining the tissue. Also, infections of mammals, particularly humans, by a virus, particularly a retrovirus such as a human immunodeficiency virus, may be effectively treated with the compounds of Formula I.

The aroylaniline compounds and related compounds of the present invention have the following formula:

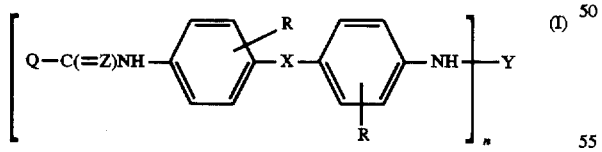

wherein R is —H, —SO$_3$.E, —CO$_2$.E, —PO(O)$_2$.2E, —NO$_2$, or a halogen;

Q is

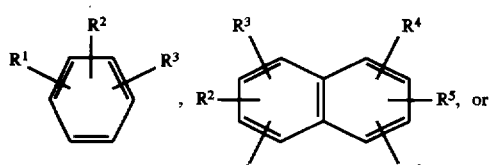

-continued

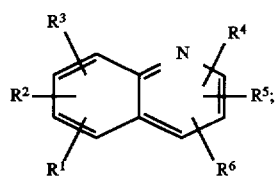

Y is

—H, —CO, —CS, 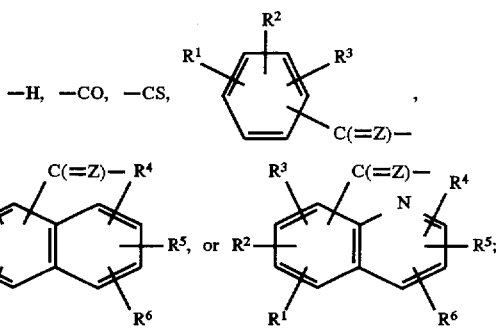

$R^1$, $R^2$, $R^3$, $R^4$, $R^5$ and $R^6$ are each independently —H, —OH, a halogen, —NH$_2$, —NHCH$_3$, —N(CH$_3$)$_2$, —CHO, CH$_3$O—, —SO$_3$.E, —NO$_2$, —CO$_2$.E, —PO(O)$_2$.2E, —CH$_2$OH, —CH$_2$SCH$_2$COR$^7$, —CH$_2$S—C$_2$H$_4$COR$^7$, —CH$_2$S—CH(CO$_2$H)CH$_2$COR$^7$, —CH$_2$S—CH(CO$_2$H)CH$_2$CO$_2$R$^7$, —CH$_2$SCH$_2$CO$_2$R$^7$, —CH$_2$SC$_2$H$_4$CO$_2$R$^7$ or

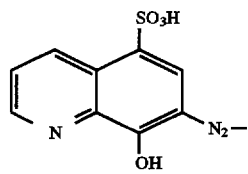

wherein E represents H, lithium, sodium, potassium, ammonium, magnesium, (HOC$_2$H$_4$)$_3$NH, (CH$_3$)$_3$NH, CH$_3$NH(C$_2$H$_4$OH)$_2$, (CH$_3$)$_4$N, or HN-methylglucamine and wherein R$^7$ is —H, methyl, ethyl, benzyl, —NH$_2$, —NHCH$_3$, or —NHC$_2$H$_5$;

X is —CHCH—, —CH$_2$CH$_2$—, —CONH—, —NHCONH—, —NHCSNH—, —S—, —SO—, —SO$_2$—, —NH—, —CH$_2$— or cyclopropyl;

Z is oxygen or sulfur; and n is 1 or 2, but when n is 1, Y is H,

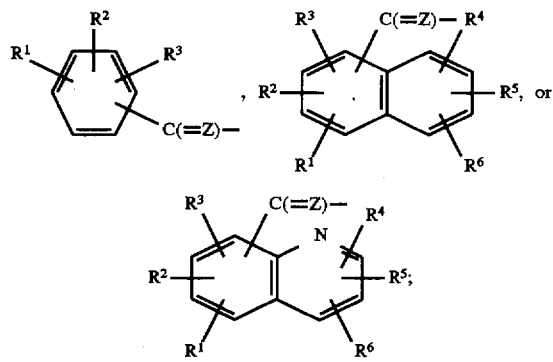

and when n is 2, Y is —CO or —CS.

The present invention also provides for a method inhibiting replication of a virus, particularly a retrovirus, and more particularly a human immunodeficiency virus, specifically HIV-1 or HIV-2 both in vitro and in vivo, by contacting cells with the aroylaniline compounds of the present invention.

The present invention further provides a method of treating a mammal, particularly a human, infected with a virus, particularly a retrovirus such as a human immunodeficiency virus, comprising administering a retrovirally effective amount of an aroylaniline compound of Formula I. Additionally, the present invention provides a method of preventing a mammal, particularly a human, from being infected with a virus, particularly a retrovirus such as a human immunodeficiency virus, comprising administering a prophylactively effective amount of an aroylaniline compound of Formula I.

The present invention also provides a method for utilizing the aroylaniline compounds of Formula I for screening and other diagnostic testing.

DETAILED DESCRIPTION OF THE INVENTION

Figure 1:
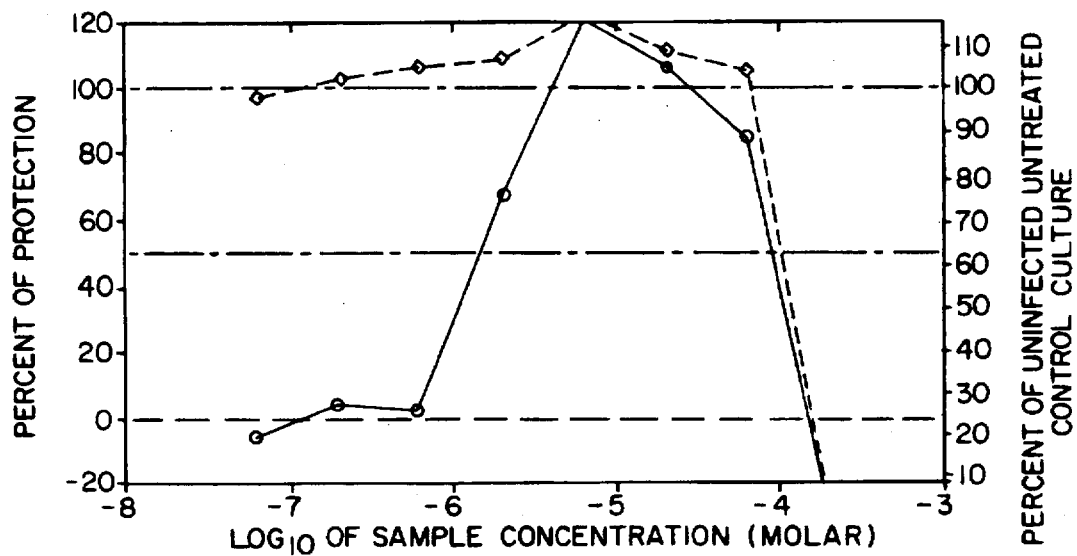
FIG. 1 depicts in vitro testing results for anti-HIV activity for the present inventive compound of Example 1.

The aroylaniline compounds and related compounds of the present invention have the following formula:

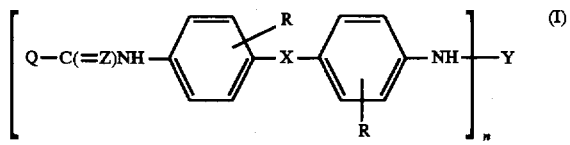

(I)

wherein R is —H, —SO$_3$.E, —CO$_2$.E, —PO(O)$_2$.2E, —NO$_2$, or a halogen;

Q is

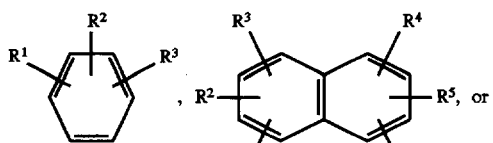

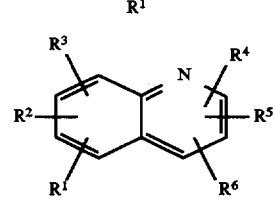

Y is

—H, —CO, —CS, 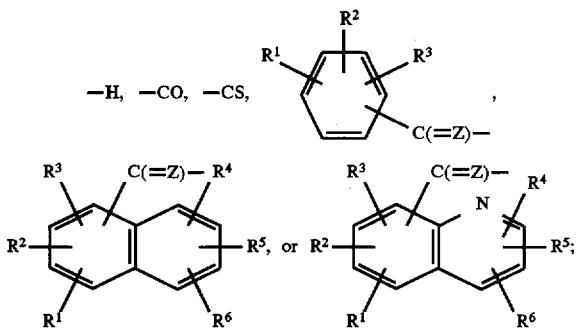

$R^1$, $R^2$, $R^3$, $R^4$, $R^5$ and $R^6$ are each independently —H, —OH, a halogen, —NH$_2$, —NHCH$_3$, —N(CH$_3$)$_2$, —CHO, CH$_3$O—, —SO$_3$.E, —NO$_2$, —CO$_2$.E, —PO(O)$_2$.2E, —CH$_2$OH, —CH$_2$SCH$_2$COR$^7$, —CH$_2$S—C$_2$H$_4$COR$^7$, —CH$_2$S—CH(CO$_2$H)CH$_2$COR$^7$, —CH$_2$S—CH(CO$_2$H)CH$_2$CO$_2$R$^7$, —CH$_2$SCH$_2$CO$_2$R$^7$, —CH$_2$SC$_2$H$_4$CO$_2$R$^7$ or

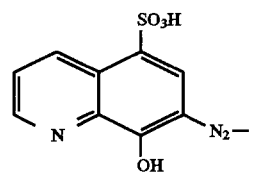

wherein E represents H, lithium, sodium, potassium, ammonium, magnesium, (HOC$_2$H$_4$)$_3$NH, (CH$_3$)$_3$NH, CH$_3$NH(C$_2$H$_4$OH)$_2$, or HN-methylglucamine and wherein R$^7$ is —H, methyl, ethyl, benzyl, —NH$_2$, —NHCH$_3$, or —NHC$_2$H$_5$;

X is —CHCH—, —CH$_2$CH$_2$—, —CONH—, —NHCONH—, —NHCSNH—, —S—, —SO—, —SO$_2$—, —NH—, —CH$_2$— or cyclopropyl;

Z is oxygen or sulfur; and n is 1 or 2, but when n is 1, Y is H,

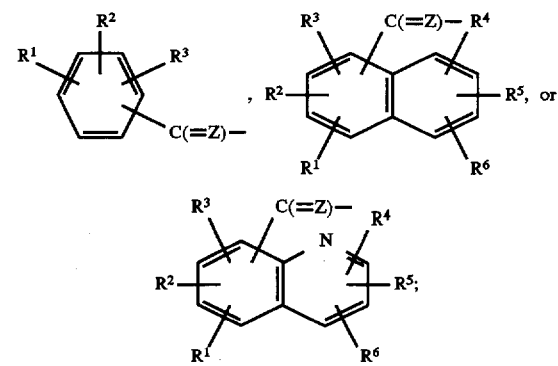

and when n is 2, Y is —CO or —CS.

Preferably, the aroylaniline compounds have the structural formulas indicated by the compounds identified in Table 1.

TABLE 1

| COMPOUND | X/+ | Q | Z | POSITION OF AMINE | R/+ | R¹/+ | R²/+ | R³/+ | R⁴/+ | R⁵/+ | R⁶/+ | Y | n | SALT |
|---|---|---|---|---|---|---|---|---|---|---|---|---|---|---|
| 1 | $C_2H_2$/1 | U | O | 7 | $SO_3^-$/2 | OH/8 | $SO_3^-$/5 | H | H | H | H | U | 1 | Na |
| 2 | $C_2H_2$/1 | U | O | 7 | $SO_3^-$/2 | OH/8 | $SO_3^-$/5 | H | H | H | H | H | 1 | Na |
| 3 | $C_2H_2$/1 | U | O | 7 | $SO_3^-$/2 | OH/8 | $SO_3^-$/5 | H | H | H | H | CO | 2 | Na |
| 4 | $C_2H_2$/1 | U | O | 7 | $SO_3^-$/2 | OH/8 | H | H | H | H | H | U | 1 | Na |
| 5 | $SO_2$/1 | U | O | 7 | $CO_2^-$/3 | OH/8 | $SO_3^-$/5 | H | H | H | H | U | 1 | K |
| 6 | $C_2H_2$/1 | U | O | 7 | $SO_3^-$/2 | OH/8 | CHO/5 | H | H | H | H | U | 1 | Na |
| 7 | $CH_2$/1 | U | O | 7 | $CO_2^-$/3 | OH/8 | $SO_3^-$/5 | H | H | H | H | U | 1 | $NH_4$ |
| 8 | $SO_2$/1 | U | O | 7 | $SO_3^-$/2 | OH/8 | $SO_3^-$/5 | H | Cl/2 | H | H | U | 1 | Li |
| 9 | $C_2H_2$/1 | U | O | 7 | $SO_3^-$/2 | OH/8 | $SO_3^-$/5 | H | Cl/4 | H | H | U | 1 | $(CH_3)_3NH$ |
| 10 | $C_2H_4$/2 | U | O | 7 | $SO_3^-$/2 | OH/8 | $CH_2OH$/5 | H | H | H | H | U | 1 | $NH_4$ |
| 11 | NHCONH/1 | U | O | 7 | $SO_3^-$/2 | OH/8 | $SO_3^-$/5 | H | $OCH_3$/4 | H | H | U | 1 | K |
| 12 | 1,2-cyclopropyl/1 | U | O | 7 | $CO_2^-$/2 | OH/8 | Cl/5 | H | H | H | H | U | 1 | $(CH_3)_4N$ |
| 13 | $C_2H_2$/1 | U | O | 7 | $SO_3^-$/2 | OH/8 | $CH_2SC_2H_4CO_2^-$/5 | H | H | H | H | U | 1 | Na |
| 14 | $C_2H_2$/1 | U | O | 7 | $SO_3^-$/2 | OH/8 | $CH_2SCH_2CO_2^-$/5 | H | H | H | H | U | 1 | Na |
| 15 | $C_2H_4$/1 | U | O | 7 | $SO_3^-$/2 | OH/8 | $CH_2S-CH(CO_2^-)CH_2CO_2^-$/5 | H | H | H | H | U | 1 | $(HOC_2H_4)_3NH$ |
| 16 | $C_2H_2$/1 | U | O | 7 | $SO_3^-$/2 | OH/8 | $CH_2S-CH_2CO_2CH_3$/5 | H | H | H | H | U | 1 | $NH_4$ |
| 17 | 1,2-cyclopropyl/1 | U | O | 7 | $SO_3^-$/2 | OH/8 | $CH_2S-CH_2CONH_2$/5 | H | H | H | H | U | 1 | Na |
| 18 | S/1 | U | O | 7 | $SO_3^-$/2 | OH/8 | $CH_2SCH_2CONHCH_3$/5 | H | H | H | H | U | 1 | Na |
| 19 | $C_2H_2$/1 | U | S | 7 | $SO_3^-$/2 | OH/8 | H | H | H | H | H | U | 1 | Na |
| 20 | $C_2H_2$/1 | U | S | 7 | $SO_3^-$/2 | OH/8 | $CH_2SCH_2CO_2^-$/5 | H | H | H | H | U | 1 | $NH_4$ |
| 21 | $C_2H_4$/1 | U | S | 7 | $SO_3^-$/2 | OH/8 | $CH_2SC_2H_4CO_2^-$/5 | H | H | H | H | U | 1 | $NH_4$ |
| 22 | $SO_2$/1 | U | S | 7 | $SO_3^-$/2 | OH/8 | $CH_2SCH_2CONH_2$/5 | H | H | H | H | U | 1 | Li |
| 23 | S/1 | U | S | 7 | $SO_3^-$/2 | OH/8 | $CH_2SCH_2CO_2CH_3$/5 | H | H | H | H | U | 1 | Li |
| 24 | $C_2H_2$/1 | N | O | 2 | $SO_3^-$/2 | OH/1 | $CH_2SC_2H_4CO_2^-$/4 | H | H | H | H | N | 1 | Na |
| 25 | $C_2H_4$/1 | N | O | 2 | $SO_3^-$/2 | OH/1 | $CH_2SCH_2CO_2^-$/4 | H | H | H | H | N | 1 | $NH_4$ |
| 26 | $C_2H_2$/1 | N | O | 2 | $SO_3^-$/2 | OH/1 | $CH_2SCH_2CO_2CH_3$/4 | H | H | H | H | N | 1 | Na |
| 27 | $C_2H_4$/1 | N | O | 2 | $SO_3^-$/2 | OH/1 | $CH_2SCH_2CONH_2$/4 | H | H | H | H | H | 1 | $(CH_3)_4N$ |
| 28 | $C_2H_2$/1 | N | O | 2 | $SO_3^-$/2 | OH/1 | $CH_2SC_2H_4CONHCH_3$/4 | H | H | H | H | H | 1 | Na |
| 29 | $C_2H_2$/1 | P | O | 1 | $SO_3^-$/2 | $CO_2^-$/2 | OH/3 | OH/6 | — | — | — | P | 1 | Na |
| 30 | $C_2H_2$/1 | P | O | 1 | $CO_2^-$/2 | $CO_2^-$/2 | OH/3 | OH/6 | — | — | — | P | 1 | Na |
| 31 | $C_2H_2$/1 | P | O | 1 | $CO_2^-$/3 | $CO_2^-$/2 | OH/3 | OH/6 | — | — | — | P | 1 | K |
| 32 | $C_2H_2$/1 | P | O | 1 | $SO_3^-$/2 | $SO_3^-$/2 | (quinoline with $SO_3^-$, $N_2$, OH)/4 | H | — | — | — | P | 1 | Na |
| 33 | $C_2H_2$/1 | P | O | 1 | $CO_2^-$/2 | $SO_3^-$/2 | (quinoline with $SO_3^-$, $N_2$, OH)/4 | H | — | — | — | P | 1 | Na |
| 34 | $C_2H_4$/1 | P | O | 1 | $SO_3^-$/2 | $SO_3^-$/2 | (quinoline with $SO_3^-$, $N_2$, OH)/4 | H | — | — | — | P | 1 | Na |

Notes: U = QUINOLINE; N = NAPHTHLENE; P = PHENYL; + = POSITION

The aroylaniline compounds of Formula I, particularly compounds 1-12 in Table 1, are prepared by reacting the requisite aromatic acid (III) with the aniline compounds (II).

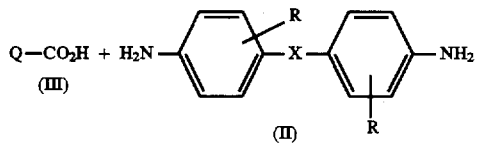

Preferably, the aromatic acid (III) is first activated by converting the acid into a symmetric anhydride, mixed anhydride, active ester, or acid chloride, by using N,N-dieyclohexylcarbodiimide (DCC) and N-hydroxybenzotriazole (HBT) as activating agents. Additional routes toward amides are well documented in Barton's *Comprehensive Organic Chemistry*, vol. II, 958, Pergamon 1979, and in T. W. Greene's *Protective Groups in Organic Chemistry*, J. Wiley & Sons, New York 1991. When using DCC and HBT as coupling agents, DMF is the preferred solvent. The reaction can be conducted at elevated temperature for shorter periods, but room temperature is preferable. Reaction times may vary from one to eight days. To assure optimal yields of the desired aroylaniline compounds and a minimum of by-products, the reaction is preferably conducted for a maximum of eight days.

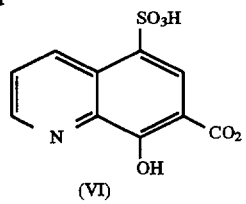

Compounds of Formula I, wherein n is 2 and Y is —CO, such as Compound 3 in Table 1, are synthesized by carbonylation of compounds I, where n is 1 and Y is H, using either phosgene, triphosgene or carbonyldiimidazole as a reagent, as shown below for the synthesis of compound 3.

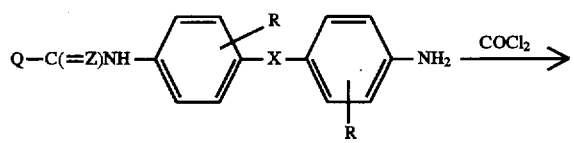

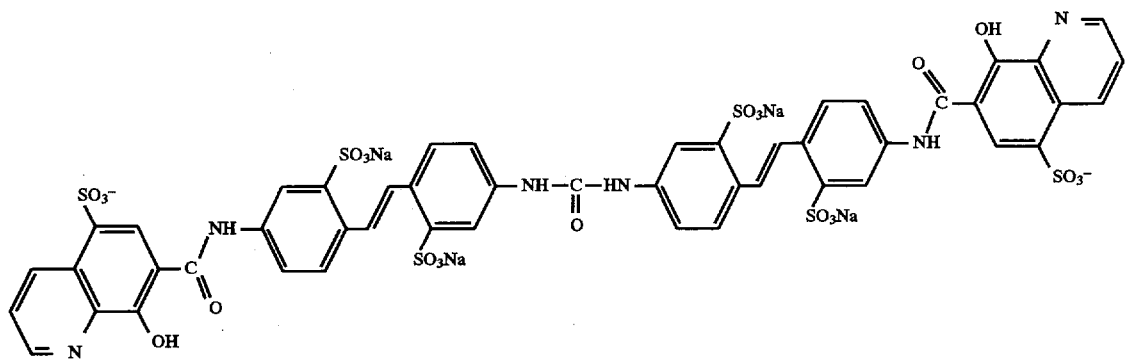

The key intermediate for quinolinoyl-substituted anilines is prepared starting with the commercially available 8-hydroxyquinoline-5-sulfonic acid (IV), which is formylated for example using the Duff reaction to furnish 8-hydroxyquinoline-7-formyl-5-sulfonic acid (V). Potassium permanganate oxidation of the product under basic conditions yields 8-hydroxyquinoline-5-sulfo-7-carboxylic acid (VI) which is then coupled with an aniline compounds (II) using HBT and DCC as activating agents to furnish the quinoline compounds of Formula I.

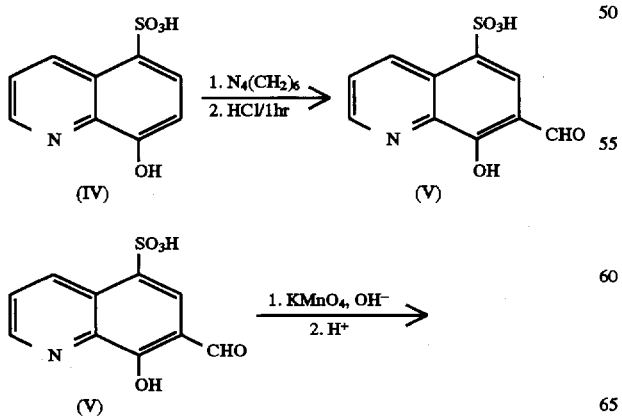

Thio-Mannich products, i.e., Formula I, (where n is 1, $R^2$ is —$CH_2SCH_2COR^7$, —$CH_2S$—$C_2H_4COR^7$, —$CH_2S$—CH($CO_2H)CH_2COR^7$, $CH_2S$—$CH(CO_2H)CH_2CO_2R^7$, and Y is phenyl, quinoline or naphthalene ring structure as defined above) are obtained by reacting compounds of Formula I, wherein at least one $R^1$–$R^6$ substituent is a hydroxy group with a hydrogen at its ortho or para position (such as compounds 13–18 in Table 1), with formaldehyde and the appropriate mercaptoalkanoic acid derivative (VII). The reaction temperature may vary from room temperature to 100° C. The reaction time may vary from one to ten hours. The preferred time is about three hours at 100° C.

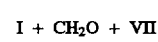

where acid derivative (VII) is $HSCH_2COR^7$, $HSC_2H_4COR^7$, $HSCH(CO_2H)CH_2COR^7$, $HSCH_2CO_2R^7$, $HSC_2H_4CO_2R^7$, $HSCH(CO_2H)CH_2CO_2R^7$, and $R^2$ is —$CH_2SCH_2COR^7$, —$CH_2S$—$CO_2H_4COR^7$, —$CH_2S$—$CH(CO_2H)CH_2COR^7$, $CH_2S$—$CH(CO_2H)CH_2CO_2R^7$, —$CH_2SCH_2CO_2R^7$, —$CH_2SC_2H_4CO_2R^7$.

Quinoline substituted compounds (I), which have a thioamide (CSNH) linkage, are prepared by reacting 8-hydroxyquinoline with o-ethylxanthic acid (potassium salt) at elevated temperatures in an autoclave to obtain 8-hydroxyquinoline-7-thioacid. The preferred temperature range is 130°–180° C. Coupling of this compound to aniline derivatives (II), in the presence of DCC/HBT yields thioamide linked quinolines, such as Compounds 19–23 in Table 1. The last step of the sequence is illustrated by the preparation of Compound 19.

Thioamides may also be prepared by reacting amides with the dimer of p-methoxyphenylthiono phosphine sulfide, Lawesson's Reagent.

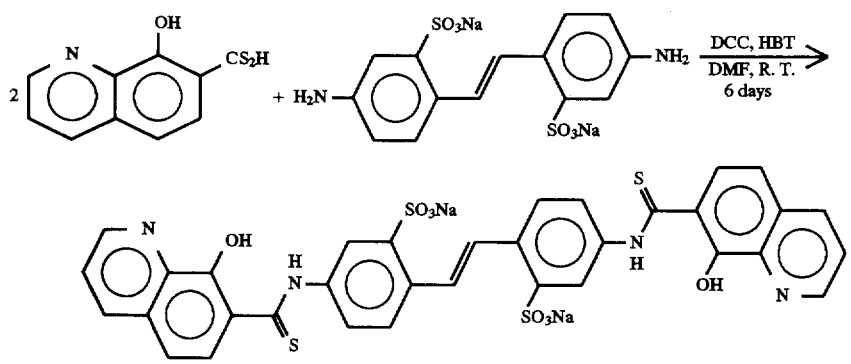

Compounds (I) which have hydroxynaphthalene groups as terminal substituents, such as Compounds 24–28 in Table 1, can be reacted with mercaptoalkanoic acids, esters or amides and formalin to give the corresponding thio-Mannich products with the carboxy-, alkoxycarbonyl- or amidoalkylthiomethyl group at the ortho(para) position (relative to the hydroxy group). The reaction time may vary from one to twelve hours at temperatures ranging from 50° to 100° C.

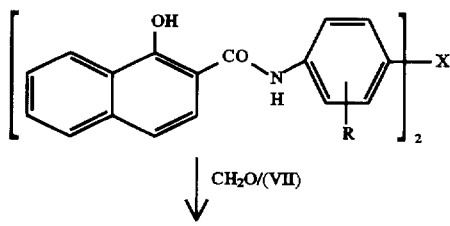

where VII is $HSCH_2COR^7$, $HSC_2H_4COR^7$, $HSCH(CO_2H)CH_2COR^7$, $HSCH_2CO_2R^7$, $HSC_2H_4CO_2R^7$, $HSCH(CO_2H)CH_2CO_2R^7$, and $R^2$ is $—CH_2SCH_2COR^7$, $—CH_2S—C_2H_4COR^7$, $—CH_2S—CH(CO_2H)CH_2COR^7$, $CH_2S—CH(CO_2H)CH_2CO_2R^7$, $—CH_2SCH_2CO_2R^7$, or $—CH_2SC_2H_4CO_2R^7$.

Acylation of 4,4'-diaminostilbene-2,2'-disulfonic acid disodium salt with 2,3-dihydroxyphthalic anhydride furnishes the ring-opened derivative, Compound 29 in Table 1, depicted below.

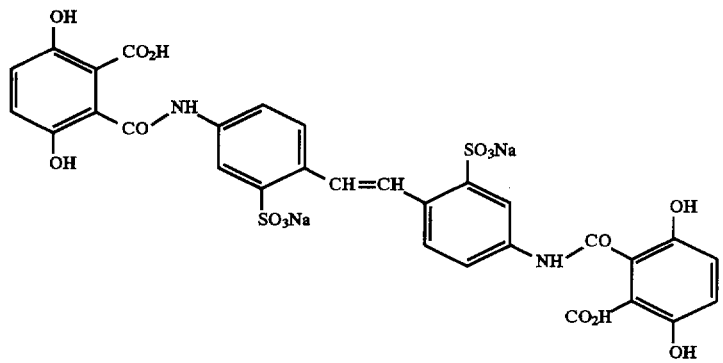

The synthesis of Compound 32 in Table 1 is depicted below.

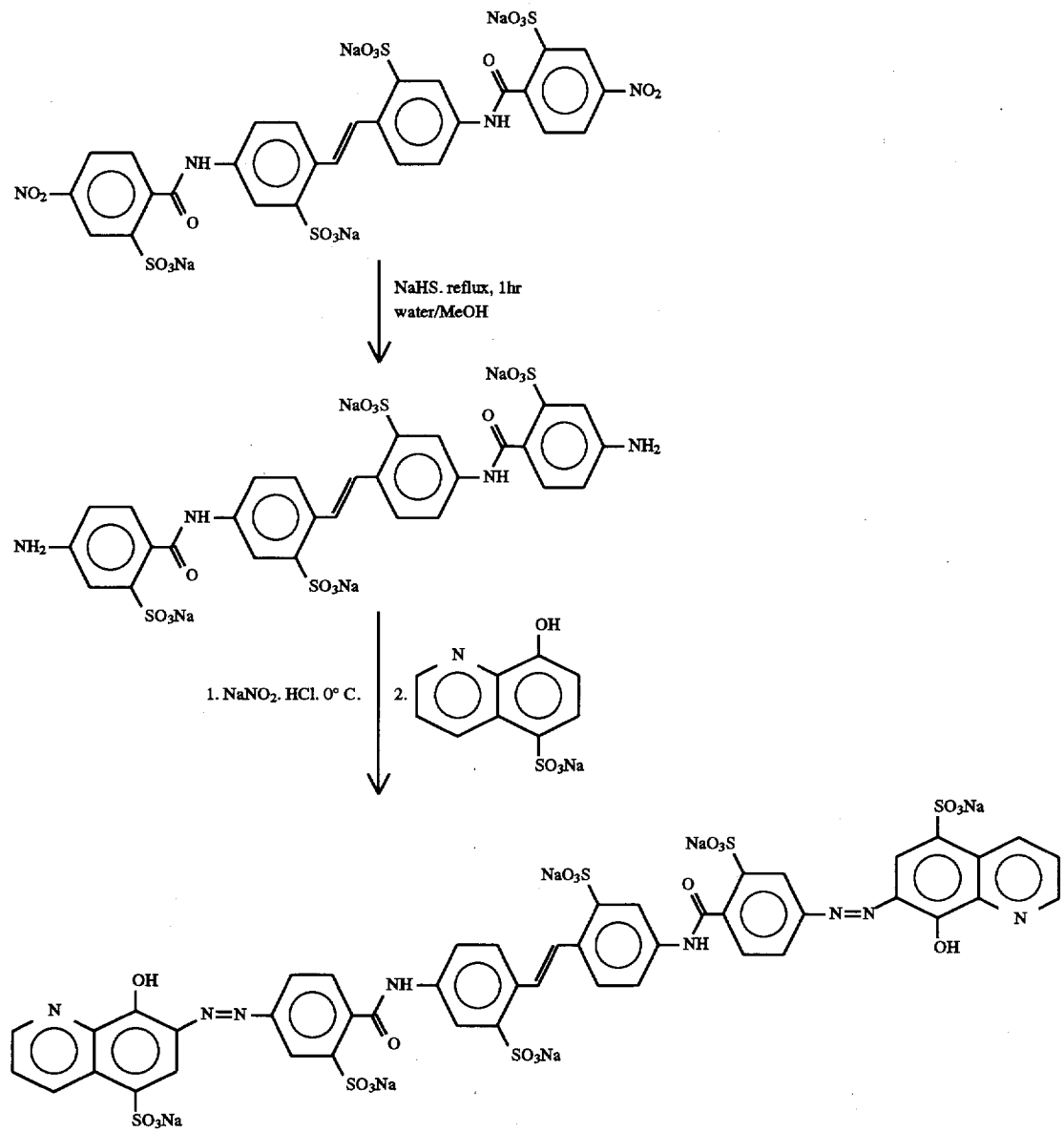

The aroylaniline compounds of the present invention act as a chemical barrier to retroviral, particularly HIV, transmission. Specifically, it is believed that the mechanism of action is that the aroylaniline compounds bind to the CD4+ amino acid region that contains a high concentration of arginine which retoviruses such as HIV typically bind to.

The aroylaniline compounds of the present invention can be used in the form of their pharmaceutically acceptable salts, can be used alone or in appropriate association, and can also be used in combination with other pharmaceutically active compounds. The active agent can be present in the pharmaceutical composition in any suitable quantity. The pharmaceutical excipients described herein, for example, vehicles, adjuvants, carriers or diluents, are well known to those who are skilled in the art, and readily available. The choice of excipient will be determined in part by the particular compound, as well as by the particular method used to administer the composition. Accordingly, there is a wide variety of suitable formulations of the pharmaceutical compositions of the present invention. The following methods and excipients are merely exemplary and are in no way limiting.

The aroylaniline compounds of the present invention can be used in vitro for diagnostic testing and other assays or screening methods well known to one of ordinary skill in the art. For example, the compounds may be used for studying viruses, particularly retroviruses.

While the method of the present invention can be practiced in vitro, it has particular usefulness in in vivo applications. As regards these applications, the present invention includes the administration to a mammal, particularly a human, of a virally effective amount, particularly a retrovirally effective amount of one or more of the aforementioned aroylaniline compounds as the active agent effective against a viral infection, such as AIDS and AIDS-related infections.

One skilled in the art will appreciate that suitable methods of administering a compound of the present invention to a mammal are available, and, although more than one route can be used to administer a particular compound, a particular route can provide a more immediate and more effective reaction than another route. The compounds may be administered in any suitable manner, including orally, buccally, sublingually, subcutaneously, intramuscularly, intravenously or rectally.

The aroylaniline compounds of the present invention can be employed in pharmaceutical compositions and used for treating viral infections, particularly retroviral infections. For example, the present inventive aroylaniline compounds can be used to treat infections by viruses, such as Hepatitis B, HTLV-1, HTLV-II, HTLV-IV, HTLV-V, HIV-1, HIV-2, HIV-3 and HIV-4, herpes simplex I, herpes simplex II, herpes zoster, Epstein-Barr virus, cytomegalo viruses and influenza.

The aroylaniline compounds employed in the present invention can be made into pharmaceutical compositions by combination with appropriate pharmaceutically acceptable carriers or diluents, and may be formulated into preparations in solid, semi-solid, liquid or gaseous forms such as tablets, capsules, granules, powders, solutions, suppositories, injections, inhalants, and aerosols in the usual ways for their respective route of administration.

In the case of oral preparations, the aroylaniline compounds can be used alone or in combination with appropriate additives to make tablets, powders, granules or capsules, e.g., with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

Furthermore, the aroylaniline compounds employed in the present invention can be made into suppositories by mixing with a variety of bases such as emulsifying bases or water-soluble bases. The suppository can include vehicles such as cocoa butter, carbowaxes and polyethylene glycols, which melt at body temperature, yet are solid at room temperature.

Formulations suitable for parenteral administration include aqueous and non-aqueous, isotonic, and sterile injection solutions. The aroylaniline compounds employed in the present invention can be formulated into preparations for injections by dissolving, suspending or emulsifying them in an aqueous or non-aqueous solvent, such as vegetable oil, synthetic aliphatic acid glycerides, esters of higher aliphatic acids or propylene glycol, and, if desired, with conventional additives such as solubilizers, isotonic agents, suspending agents, emulsifying agents, stabilizers, thickening agents and preservatives. Solution forms can include buffers, such as acetate and phosphate, toxicity adjusting agents, such as sodium chloride, pH adjusting agents, such a HCl and phosphoric acid, bactericides, solutes that render the solution isotonic with the blood of the intended recipient, and the like.

Extracorporeal injection solutions and suspensions can be prepared from sterile powders, granules and tablets of the kind previously described.

In the case of inhalations or aerosol preparations, the aroylaniline compounds employed in the invention in the form of a liquid or minute powder can be utilized in an aerosol container with gas or liquid propellants, such as dichlorofluoromethane, propane, nitrogen, and the like, and, if desired, together with conventional adjuvants such as humidifying agents. They can also be formulated as pharmaceuticals for non-pressured preparations such as in a nebulizer or an atomizer.

Unit dosage forms for oral administration such as syrups, elixirs, and suspensions wherein each dosage unit, e.g., teaspoonful or tablespoonful, contains a predetermined amount of the aroylaniline compounds. employed in the present invention can be by a pharmaceutically acceptable carrier, such as Sterile Water for Injection, USP, or normal saline.

The term "unit dosage form" as used herein refers to physically discrete units suitable as unitary dosages for human and animal subjects, each unit containing a predetermined quantity of the aroylaniline compounds calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the host.

The amount of aroylaniline compound of the present invention to be used varies according to the degree of infection encountered and the stage of the disease. A suitable dosage is that which will result in concentration of the aroylaniline compound in blood and/or tissue harboring virus which is known to inhibit the virus, e.g., about $10^{-9}$M to $10^{-4}$M, more preferably $10^{-8}$M to $10^{-6}$M. The preferred dosage is that amount sufficient to beneficially affect a host and possibly render the host asymptomatic to the particular viral infection. For example, the dosage amount can vary between 0.01–5 mg/kg body weight administered 1–5 times daily. The dose may vary when the compounds are used prophylactically.

Any necessary adjustments in dose can be readily made to meet the severity of the infection and adjusted accordingly by the skilled practitioner.

The following examples further illustrate the present invention but, of course, should not be construed as in any way limiting its scope.

EXAMPLES

Materials and Methods for Synthesizing Aroylaniline Compounds

In each of the following examples, melting points were determined with a Kofler hot stage microscope and are corrected. All temperatures are in degrees centigrade. NMR spectra were determined with a Varian Gemini-300 (300 MHz) spectrometer. Chemical shifts ($\delta$) were reported relative to the appropriate deuterated standard. Mass spectra were recorded on a VG Analytical 70-SE mass spectrometer equipped with an 11-205 J data system. IR spectra were recorded on a Nicolet 520 FT-IR spectrometer. UV spectra were recorded on a Shimadzu UV-VIS scanning spectrometer. Elemental analysis was performed by Atlantic Microlab, Inc., Norcross, Ga.

Example 1

This Example illustrates the synthesis of the aroylaniline compound, 4,4'-di(8-hydroxy-5-sulfo-7-quinolinecarboxyamido)stilbene-2,2'disulfonic acid tetrasodium salt, Compound 1 as shown in Table 1.

A. Synthesis of 7-formyl-8-hydroxyquinoline-5-sulfonic acid.

8-Hydroxyquinoline-5-sulfonic acid monohydriate (0.015 mol, 3.65 g), hexamethylenetetramine (0.225 mol, 21.0 g) and acetic acid (750 mL) were stirred and heated at 97°–100° C. for 6 hrs. After cooling, acetic acid was removed under reduced pressure, and the residue was treated with acetone (1 L) to give a precipitate which was filtered off and washed with additional acetone. Water (30 mL) and concentrated hydrochloric acid (15 mL) were then added to the solid. The resulting solution was refluxed for 2 hours. Then, the mixture was concentrated under reduced pressure and left for crystallization. The solid was filtered off, washed with water and dried to give pure 7-formyl-8-hydroxyquinoline-5-sulfonic acid in 45% yield.

m.p. 286°–288° C.

$^1$H NMR (DMSO-$d_6$) δ [ppm]: 10.54 (s, 1H, H-e) 9.22 (dd, J=8.7; 1.5 Hz, 1H, H-a) 8.99 (dd, J=4.5; 1.5 Hz, 1H, H-c) 8.17 (s, 1H, H-d) 7.84 (dd, J=8.7; 4.5 Hz, 1H, H-b)

IR (KBr) $v_{max}$ [cm$^{-1}$]: 3442, 3109, 2926, 2855, 1657, 1611, 1594, 1552, 1401, 1330, 1282, 1244, 1176, 1126, 1045, 987, 942, 897, 828, 765, 743, 634, 591.

B. Oxidation of 7-formyl-8-hydroxyquinoline-5-sulfonic acid

The 7-formyl-8-hydroxyquinoline-5-sulfonic acid (15 mmol, 3.80 g) was dissolved in sodium carbonate solution (34.5 mmol, 3.66 g in 200 mL of $H_2O$). The solution was stirred and heated at 52° C. (oil bath). Then to the hot solution potassium permaganate (37.5 mmol, 5.94 g) was added. The temperature was increased to 68° C. The stirring and heating (60°–65° C.) was continued for 55 minutes. After that time the reaction mixture was filtered, and the solid was washed with sodium carbonate solution followed by water. The filtrate was concentrated under reduced pressure, acidified with 50% sulfuric acid (pH 3) and left for crystallization. The precipitate was filtered off, washed with a small amount of water and dried to give 1.96 g of 7-carboxy-8-hydroxyquinoline-5-sulfonic acid (48.5%).

m.p. 289°–291° C.

$^1$H NMR (DMSO-$d_6$) δ [ppm]: 9.39 (dd, J=8.7; 1.5 Hz, 1H, H-a) 8.89 (dd, J=4.5; 1.5 Hz, 1H, H-c) 8.33 (s, 1H, H-d) 7.88 (dd, J=8.7; 4.5 Hz, 1H, H-b) IR (KBr) $v_{max}$ [cm$^{-1}$]: 3408, 3095, 2922, 1673, 1611, 1601, 1547, 1474, 1383, 1310, 1228, 1184, 1159, 1109, 1052, 965, 823, 791, 771, 701, 665, 617, 598.

C. Synthesis of 4,4'-di(8-hydroxy-5-sulfo-7-quinolinecarboxyamido)stilbene-2,2'-disulfonic acid tetrasodium salt To a solution of 4,4'-diaminostilbene-2'-disulfonic acid disodium salt (2.5 mmol, 1.036 g) in DMF (170 mL) a solution of 7-carboxy-8-hydroxyquinoline-5-sulfonic acid monosodium salt (5.0 mmol, 1.456 g) in DMF (650 mL) was added. To the mixture, 1-hydroxybenzotriazole (HBT) (15.0 mmol, 2.027 g) was added followed by 1,3-dicyclohexylcarbodiimide (DCC) (20.0 mmol, 4.127 g). The reaction mixture was stirred at room temperature for 8 days. After that time the reaction solution was concentrated under reduced pressure. The precipitate was removed by filtration. The filtrate was evaporated in vacuo. Water was added to the residue and the mixture was evaporated under reduced pressure. Next the residue was extracted with chloroform (3×). Insoluble material was filtered off and treated with methanol, with its pH being adjusted to 8. A small amount of insoluble material was removed by filtration. The methanol solution was used for fractionation on Sephadex LH-20 column using methanol as the eluent. This technique allowed for the separation of pure diamide in 20% yield. The fractionation was repeated for non-homogeneous fractions containing the desired compound together with a small amount of monoamide. Finally, the pure diamide was separated from the reaction mixture in 25% yield. Its substituents and their position of attachment are shown in Table 1, under Compound 1.

m.p. >300° C.

$^1$H NMR ($D_2O$) δ [ppm]: 8.75 (br d, J=8.1 Hz, 2H, H-a) 8.67 (br d, J=3.9 Hz, 2H, H-c) 8.54 (s, 2H, H-d) 8.22 (d, J=2.1 Hz, 2H, H-e) 7.89 (d, J=8.7 Hz, 2H, H-g) 7.86 (s, 2H, H-h) 7.78 (dd, J=8.4; 1.8 Hz, 2H, H-f) 7.56 (dd, J=8.1; 4.2 Hz, 2H, H-b).

IR (KBr) $v_{max}$ [cm$^{-1}$]: 3443, 2926, 2855, 1641, 1580, 1530, 1499, 1451, 1405, 1306, 1190, 1113, 1080, 1061, 1042, 1025, 761, 703, 624.

UV ($H_2O$) $v_{max}$ [nm]: 204, 244, 277, 367.

Anal. ($C_{34}H_{20}N_4Na_4O_{16}S_4$×$9H_2O$) C, H, N, S.

Example 2

This Example illustrates the synthesis of the aroylaniline compound, 4-amino-4'-(8-hydroxy-5-sulfo-7-quinolinecarboxyamido)stilbene-2,2'-disulfonic acid trisodium salt, Compound 2 as shown in Table 1. To a solution of 4,4'-diaminostilbene-2,2'-disulfonic acid disodium salt (0.5572 mmol, 0.234 g) in DMF (35 mL) a solution of 7-carboxy-8-hydroxyquinoline-5-sulfonic acid monosodium salt (1.114 mmol, 0.324 g) in DMF (65 mL) was added. To the mixture 1-hydroxybenzotriazole (HBT) (1.332 mmol, 0.180 g) and then 1,3-dicyclohexylcarbodiimide (DCC) (2.228 mmol, 0.360 g) were added. The reaction mixture was refluxed under nitrogen for 3 days. Then, insoluble material was filtered off to give 0.073 g of the product of 7-carboxy-8-hydroxyquinoline-5-sulfonic acid monosodium salt self-esterification. The filtrate was evaporated under reduced pressure. Water was added to the residue and insoluble material was filtered off. The filtrate was concentrated in vacuo and the pH of solution was adjusted to 9. The solvent was removed under reduced pressure. The residue was treated with methanol, insoluble material was removed by filtration, and the filtrate was concentrated under reduced pressure and fractionated on Sephadex LH 20 column using methanol as eluent. Fractionation was repeated for non-homogeneous fractions containing product. This technique allowed for the separation of the pure monoamide, Compound 2, in 42% yield (0.160 g).

m.p. >300° C.

$^1$H NMR ($D_2O$) δ [ppm]: 8.77 (br d, J=8.4 Hz, 1H, H-a) 8.67 (br d, J=4.2 Hz, 1H, H-c) 8.52 (s, 1H, H-d) 8.16 (d, J=2.1 Hz, 1H, H-e) 7.76 (m, 4H, H-f, H-g, H-h, H-i) 7.65 (d, J=8.4 Hz, 1H, H-k) 7.59 (dd, J=8.4; 4.2 Hz, 1H, H-b) 7.21 (d, J=2.4 Hz, 1H, H-j) 6.88 (dd, J=8.4; 2.4 Hz, 1H, H-1).

IR (KBr) $v_{max}$ [cm$^{-1}$]3444, 2956, 2925, 2854, 1635, 1605, 1577, 1526, 1498, 1456, 1449, 1405, 1307, 1188, 1140, 1113, 1083, 1049, 1025, 797, 764, 730, 706, 622.

Anal. ($C_{24}H_{16}N_3Na_3O_{11}S_3$×$5H_2O$) C, H, N, S.

Example 3

This Example illustrates the synthesis of 1,3-di[2,2'-disulfo-4(8-hydroxy-5-sulfo-7-quinoline)]stilbene urea, hexasodium salt, Compound 3 as shown in Table 1.

A solution of the monoamide from Example 2 above (0.07 mmol, 0.048 g) and triethylamine (0.2 mL) in DMF (50 mL) was added dropwise over 20 minutes to a solution of triphosgene (0.14 mmol, 0.042 g) in DMF (5 mL) stirred at 5°–10° C. Then, the reaction mixture was stirred and heated at 120° C. for 6 hours followed by evaporation under reduced pressure. The solid was treated with methanol, and the pH of the methanol solution was adjusted to 8. The material was filtered, and filtrate was concentrated and used for fractionation on Sephadex LH-20 column, with the eluent being methanol. All fractions were analyzed by $^1$H NMR spectroscopy. This technique allowed for the obtaining of the desired product, Compound 3.

m.p. >300° C.

$^1$H NMR (D$_2$O) δ [ppm]: 8.75 (br d, J=8.1 Hz, 2H, H-a) 8.68 (br d, J=3.0 Hz, 2H, H-c) 8.53 (s, 2H, H-d) 8.20 (br s, 2H, H-e) 7.83, 7.59 (2 m, 16H, H-b, H-f-H-l).

IR (KBr) $v_{max}$ [cm−1]: 3439, 2961, 2926, 2850, 1735, 1660, 1460, 1397, 1193, 1139, 842, 631.

Example 4

This Example illustrates the synthesis of the aroylaniline compound, 4,4'-di(8-hydroxy-7-quinolinecarboxyamido) stilbene-2,2'-disulfonic acid disodium salt, Compound 4 as shown in Table 1.

A. Carboxylation of 8-hydroxyquinoline

Potassium salt of 8-hydroxyquinoline (25 mmol, 4.58 g), DMF (50 mL) and an excess of dry ice were heated in a pressure reactor at 120° C. for 12 hours. After cooling, water (150 mL) was added to the reaction mixture. The insoluble material was filtered off, and the filtrate was evaporated under reduced pressure. To the residue, water was added again, and additional insoluble material was collected by filtration. The filtrate was acidified to pH 4 with concentrated hydrochloric acid. The precipitate was filtered off, washed with water and dried to give 7-carboxy-8-hydroxyquinoline in 30.4% yield (1.44 g).

m.p. 264°–266° C.

$^1$H NMR (DMSO-d$_6$) δ [ppm]: 8.91 (dd, J=4.8; 1.5 Hz, 1H, H-a) 8.61 (dd, J=8.4; 1.5 Hz, 1H, H-c) 7.91 (d, J=8.4 Hz, 1H, H-e) 7.80 (dd, J=8.4; 4.5 Hz, 1H, H-b) 7.31 (d, J=8.7 Hz, 1H, H-d).

IR (KBr) $v_{max}$ [cm$^{-1}$] 3429, 3081, 2932, 1644, 1589, 1549, 1480, 1458, 1420, 1383, 1333, 1203, 1150, 1114, 936, 874, 846, 830, 800, 763, 690, 644, 600.

B. Synthesis of 4,4'-di(8-hydroxy-7-quinolinecarboxyamido)stilbene-2,2'-disulfonic acid disodium salt To a solution of 4,4'-diaminostilbene-2,2'-disulfonic acid disodium salt (2.5 mmol, 1.036 g) in DMF (170 mL) a solution of 8-hydroxyquinoline-7-carboxylic acid (5.0mmol, 0.946 g) in DMF (140 mL) was added. To the mixture, 1-hydroxybenzotriazole (HBT) (6.0 mmol, 0.811 g) was added followed by 1,3-dicyclohexylcarbocilmide (DCC) (12.0 mmol, 2.476 g). The reaction mixture was stirred at room temperature for 6 days. Then, the solution was concentrated under reduced pressure. The precipitate was filtered off. The filtrate was evaporated in vacuo. To the residue, water and methanol (1:4) were added, and the pH was adjusted to 8. The insoluble material was filtered off, and the filtrate was evaporated under reduced pressure. The residue was extracted with choloroform (3×). The solid was collected by filtration, and treated with methanol. Insoluble material was filtered off and dried to give 0.8 g of pure, desired diamide. The methanol solution was used for fractionation on a Sephadex LH-20 column, with the eluent being methanol. This method allowed for the separation of an additional 0.59 g pure diamide (yield 73.5%) and traces of monoamide.

m.p. >300° C.

$^1$H NMR (D$_2$O) δ [ppm]: 8.55 (d, J=3.0 Hz, 2H, H-a) 8.16 (d, J=2.1 Hz, 2H, H-f) 7.98 (br d, J=8.1 Hz, 2H, H-c) 7.78 (m, 6H, H-e, H-h, H-i) 7.61 (dd, J=8.4; 2.1 Hz, 2H, H-g) 7.33 (dd, J=8.4; 4.2 Hz, 2H, H-b) 6.79 (d, J=8.7 Hz, 2H, H-d).

IR (KBr) $v_{max}$ [cm$^{-1}$]3452, 2958, 2925, 2854, 1635, 1590, 1578, 1527, 1503, 1491, 1453, 1404, 1304, 1218, 1186, 1134, 1109, 1081, 1024, 825, 796, 779, 738, 711, 630.

Anal. (C$_{24}$H$_{22}$N$_4$Na$_2$O$_{16}$S$_2$×6H$_2$O) C, H, N, S

Examples 5–12

Following the procedures set forth in Example 1 and acylating amine (II) with the appropriate, activated acid (III), the quinoline compounds of Compounds 5–12 as shown in Table 1 are obtained.

Example 13

This Example illustrates the synthesis 4,4'-di[5-(2-carboxyethylthiomethyl)-8-hydroxy-7-quinolinecarboxyamido]stilbene-2,2'-disulfonic acid tetrasodium salt, Compound 13 as shown in Table 1, by 2-carboxyethylthiomethylation of the diamide of Example 4.

The above diamide, Compound 4, (0.3 mmol, 0.227 g), 3-mercaptopropionic acid (0.63 mmol, 0.0669 g), formalin (0.66 mmol, 0.0198 g), and an aqueous solution of NaOH (1.23 mmol, 0.0492 g/3 mL of H$_2$O) were refluxed under nitrogen for 1.5 hours. Then, more formalin (0.33 mmol, 0.01 g) was added, and refluxing was continued for 30 minutes. After cooling, a very small amount of insoluble material was filtered off. The filtrate was evaporated under reduced pressure. The residue was treated with methanol, and the pH of the solution was adjusted to 8. A methanol soluble material was used for fractionation on a Sephadex LH-20 column, with the eluent being methanol. This technique allowed the separation of the pure product, Compound 13, in 51.5% yield (0.16 g).

m.p. >300° C.

$^1$H NMR (D$_2$O) δ [ppm]: 8.55 (br d, J=3.3 Hz, 2H, H-a) 8.22 (br s, 2H, H-e) 8.12 (br d, J=8.4 Hz, 2H, H-c) 7.69 (s, 2H, H-h) 7.54 (d, J=8.7 Hz, 2H, H-g) 7.46 (s, 2H, H-d) 7.39 (m, 4H, H-b, H-f) 3.60 (s, 4H, H-i) 2.53 (t, J=7.2 Hz, 4H, H-j) 2.31 (t, J=7.2 Hz, 4H, H-k).

IR (KBr) $v_{max}$ [cm$^{-1}$]3449, 2924, 2860, 1636, 1576, 1544, 1527, 1504, 1491, 1458, 1399 1310, 1217, 1181, 1141, 1080, 1024, 824, 769, 735, 707, 629.

Examples 14–18

Following the procedure of Example 13 and reacting the diamide of Example 4 having the appropriate X-substituents with formaldehyde and the appropriate mercaptoalkanoic acid, mercaptoalkanoic acid ester or mercaptoalkanoic acid amide, the quinoline compounds of Compounds 14–18 were obtained.

Example 19

This Example illustrates the synthesis of the aroylaniline compound, 4,4'-di(8-hydroxy-7-quinolinethioamido) stilbene-2,2'-disulfonic acid disodium salt, Compound 19 shown in Table 1.

A. Synthesis of 7-thiocarboxy-8-hydroxyquinoline

A mixture of 8-hydroxyquinoline (0.055 mol, 8.0 g) and O-ethylxanthic acid potassium salt (0.056 mol, 9.0 g) in abs. EtOH (20 mL) was placed in a pressure reactor and heated at 160° C. for 40 hours. After cooling, the reaction mixture was washed with a small amount of EtOH. The insoluble material was filtered off and treated with aqueous hydrochloric acid. The insoluble thioacid was separated by filtration and purified by heating with barium carbonate in water. The mixture was filtered off, the filtrate was acidified with hydrochloric acid, and precipitate was collected by filtration to give 7-thiocarboxy-8-hydroxyquinoline (2.61 g) in 18.4% yield.

m.p. 174°–175° C.

$^1$H NMR (DMSO-d$_6$) δ [ppm]: 9.06 (m, 2H, H-a, H-c) 9.00 (d, J=9.0 Hz, 1H, H-e) 8.06 (dd, J=8.4; 5.4 Hz, 1H, H-b) 7.58 (d, J=9.0 Hz, 1H, H-d).

IR (KBr) $v_{max}$ [cm$^{-1}$]: 3471, 3090, 3064, 3038, 2965, 2922, 1630, 1606, 1585, 1541, 1499, 1474, 1417, 1402, 1373, 1319, 1287, 1242, 1225, 1197, 1176, 1138, 1111, 1049, 1013, 997, 982, 972, 874, 824, 811, 794, 780, 766, 718, 670.

B. Synthesis of 4,4'-di(8-hydroxy-7-quinolinethioamido) stilbene-2,2'-disulfonic acid disodium salt To a solution of 4,4'-diaminostilbene-2,2'-disulfonic acid disodium salt (1.0 mmol, 0.414 g) in DMF (70 mL) a solution of 8-hydroxyquinoline-7-thiocarboxylic acid (2.0 mmol, 0.443 g) in DMF (330 mL) was added. To the mixture, 1-hydroxybenzotriazole (HBT) (2.4 mmol, 0.324 g) was added followed by 1,3-dicyclohexylcarbodiimide (DCC) (4.8 mmol, 0.990 g). The reaction mixture was stirred at room temperature for 6 days. Then, the solution was evaporated under reduced pressure. To the residue, water and methanol (1:4) were added, and the pH was adjusted to 8. The insoluble material was filtered off, and the filtrate was evaporated under reduced pressure. The residue was extracted with chloroform (3×). The solid was collected by filtration and treated with methanol. The methanol solution was used for fractionation on a Sephadex LH-20 column, with the eluent being methanol. The fractions containing the pure, desired product of Compound 19 were combined and evaporated under reduced pressure (yield 17%).

m.p. >300° C.

$^1$H NMR ($D_2O$) δ [ppm]: 8.55 (dd, J=4.2; 1.5 Hz, 2H, H-a) 8.16 (d, J=2.1 Hz, 2H, H-e) 7.98 (dd, J=8.4; 1.5 Hz, 2H, H-c) 7.78 (m, 6H, H-e, H-h, H-i) 7.61 (dd, J=8.4; 2.1 Hz, 2H, H-g) 7.33 (dd, J=8.4; 4.5 Hz, 2H, H-b) 6.79 (d, J=8.7 Hz, 2H, H-d).

IR (KBr) $v_{max}$ [cm$^{-1}$]: 3467, 2923, 2855, 1635, 1591, 1527, 1502, 1490, 1452, 1403, 1303, 1214, 1183, 1132, 1109, 1079, 1023, 891, 824, 796, 779, 737, 711, 629.

Examples 20–23

Following the procedure set forth in Example 19 and reacting the appropriate dithioamides with formaldehyde and the appropriate mercaptoalkanoic acid, mercaptoalkanoic acid ester or mercaptoalkanoic acid amide, the quinoline Compounds 20–23 were obtained.

Example 24

This Example illustrates the synthesis of the aroylaniline derivative, 4,4'-di[4-(2-carboxyethylthiomethyl)-1-hydroxy-2-naphthamido]stilbene-2-2'-disulfonic acid tetrasodium salt, Compound 24 as shown in Table 1.

A. Synthesis of 4,4'-di(1-hydroxy-2-naphthamido)stilbene-2-2'-disulfonic acid disodium salt To a solution of 4,4'-diaminostilbene-2,2'-disulfonic acid disodium salt (2.0 mmol, 0.829 g) in DMF (140 mL) a solution of 1-hydroxy-2-naphthoic acid (4.0mmol, 0.753 g) in DMF (60 mL) was added. To the mixture, 1-hydroxybenzotriazole (HBT) (5.0 mmol, 0.676 g) was added followed by 1,3-dicyclohexylcarbodiimide (DCC) (10 mmol, 2.060 g). The reaction mixture was stirred at room temperature for 7 days. Then, the precipitate was filtered off, and the filtrate was evaporated under reduced pressure. To the residue, water was added, and the solvent was removed in vacuo. Next, the residue was extracted with chloroform (3×). The solid was collected by filtration and treated with methanol, and the pH of the solution was adjusted to 8. The methanol solution was concentrated under reduced pressure and used for fractionation on a Sephadex LH-20 column, with the eluent being methanol. This technique allowed for the separation of the pure desired diamide in 49% yield (0.74 g).

m.p. >300° C.

$^1$H NMR ($D_2O$) δ [ppm]: 8.26 (m, 2H, H-a) 8.10 (d, J=2.1 Hz, 2H, H-g) 7.75 (m, 4H, H-f, H-j) 7.70 (d, J=8.7 Hz, 2H, H-i) 7.57 (m, 2H, H-d) 7.52 (dd, J-8.7; 2.1 Hz, 2H, H-h) 7.34 (m, 4H, H-b, H-c) 6.90 (d, J-9.0 Hz 2H, H-e)

IR (KBr) $v_{max}$ [cm$^{-1}$]: 3439, 2924, 2854, 1631, 1594, 1525, 1505, 1469, 1392, 1359, 1300, 1247, 1208, 1082, 1026, 809, 790, 761, 726, 707, 632, 542.

4,4'-di[4-(2-carboxyethylthiomethyl)-1-hydroxy-2-naphthamido]stilbene-2,2'-disulfonic acid tetrasodium salt The above diamide (0.3 mmol, 0.226 g), 3-mercaptopropionic acid (0.63 mmol, 0.0669 g), formalin (0.66 mmol, 0.0198 g), and aqueous solution of NaOH (1.23 mmol, 0.0492 g/3 mL of $H_2O$) were refluxed under nitrogen for 1.5 hours. Then, more formalin (0.33 mmol, 0.01 g) was added and refluxing was continued for a further 30 minutes. After cooling, a small amount of insoluble material was filtered off. The filtrate was evaporated under reduced pressure. The residue was treated with methanol, and the pH of the solution was adjusted to 8. Methanol soluble material was used for fractionation on a Sephadex LH-20 column, with the eluent being methanol. This method allowed for the separation of the pure Compound 24 in 41.9% yield (0.13 g).

m.p. >300° C.

$^1$H NMR ($D_2O$) δ [ppm]: 8.32 (br d, J=7.8 Hz, 2H, H-a) 8.17 (d, J=2.4 Hz, 2H, H-f) 7.86 (br d, J=8.1 Hz, 2H, H-d) 7.75 (m, 4H, H-h, H-i) 7.63 (m, 4H, H-e, H-g) 7.53 (m, 2H, H-b) 7.41 (m, 2H, H-c) 3.94 (s, 2H, H-j) 2.62 (t, J=7.2 Hz, 2H, H-k) 2.38 (t, J=7.2 Hz, 2H, H-l).

IR (KBr) $v_{max}$ {cm$^{-1}$]: 3558, 3380, 2924, 2854, 1632, 1576, 1524, 1490, 1427, 1399, 1308, 1193, 1140, 1081, 1026, 764, 727, 708, 627.

Examples 25–28

Following the procedure of Example 24 and reacting the appropriate diamides with formaldehyde, and the appropriate mercaptoalkanoic acid, mercaptoalkanoic acid ester or mercaptoalkanoic acid amide, the napththalene Compounds 25–28 are obtained.

Example 29

This Example illustrates the synthesis of the aroylaniline compound, 4,4'-di(2-carboxy-3,6-dihydroxybenzamido) stilbene-2,2'-disulfonic acid disodium salt, Compound 29 as shown in Table 1.

A. Hydrolysis of 2,3-dicyanohydroquinone 2,3-Dicyanohydroquinone (29 mmol, 4.7 g) was mixed into 50% KOH (40 mL). The mixture was heated under nitrogen to reflux for 1.5 hours, then cooled to room temperature. The mixture was neutralized with aqueous $H_2SO_4$ and then extracted with ethyl acetate (5×100 mL). Evaporation of the solvent and then careful crystallization from water gave the diacid, mp 216°–219° C. (dec). Yield 3.0 g (52%). $^1$H-NMR (DMSO, ppm) 6.8 (s, 1H). FT-IR (KBr, cm$^{-1}$) 3249, 1706, 1667, 1450, 1192.

B. Anhydride Formation

The above diacid (1.0 g) was heated in a vacuum sublimation apparatus to 230° C. using tap water as the cooling source and an aspirator vacuum. The sublimed material was a sulfur yellow solid which was recrystallized from benzene. Yield was virtually quantitative. $^1$H-NMR (DMSO, ppm) 7.2 (s, 1H). FT-IR (KBr, cm$^{-1}$) 3600, 1827, 1751, 1490, 1385, 1306, 1197, 894. EIMS: 180 (100), 162 (75), 136 (21), 134 (519).

C. Condensation 4,4'-Diaminostibene-2,2' disulfonic acid disodium salt (0.4 mmol, 0.1 g) was stirred in DMF (20 mL) containing 4

Å molecular sieves overnight. Afterwards, the anhydride (0.16 g) from Part B above was added, and the mixture was stirred at 70° C. for 2 hours. After cooling and filtering, acetone was added, and the solid was collected and washed with copious amounts of acetone. After addition to 0.044 g of NaHCO$_3$ in 10 mL of water, the crude material was lyophilized to give the diamide of Compound 29, as shown in Table 1, as a light brown powder. $^1$H-NMR (DMSO, ppm) 9.82 (s, 1H), 8.18 (d, 1H, J=2 Hz), 7.99 (s, 1H), 7.63 (dd, 1H, J=2, 8 Hz), 7.50 (d, 1H, J=8 Hz), 6.72 (d, 1H, J=8 Hz), 6.55 (d, 1H, J=8 Hz). FT-IR (KBr, cm$^{-1}$) 3400 (B), 1631, 1589, 1384, 1083, 1026, 632.

Examples 30–31

Following the procedure set forth in Example 29 and reacting the appropriate aniline (II) with the anhydride of Example 29, Part B, Compounds 30–31 were obtained.

Example 32

This Example illustrates the synthesis of the aroylaniline compound, N,N'-Bis(4-amino-2-sulfobenzoyl)-4,4'-diaminostilbene-2,2-disulfonic acid tetrasodium salt, Compound 32 as shown in Table 1.

A. N,N'-Bis(4-nitro-2-sulfobenzoyl)-4,4'-diaminostibene-2,2'-disulfonic Acid Testrasodium Salt 4-Nitro-2-methylsulfonate benzoyl chloride (0.6 g, 2.0 mmol) was dissolved in ice-cold dry acetonitrile (15 ml). This solution was added dropwise to a solution of 4,4'-diaminostilbene-2,2'-disulfonic disodium salt (504 mg, 1.0 mmol) in water (25 ml) at 0° C. The reaction mixture was carefully kept at pH 7 with the addition of a dilute sodium hydroxide solution and stirred for two hours in an ice bath. A small amount of insoluble materials was filtered off, and the clear yellow solution was freeze-dried to give a mixture containing mainly the product. Gel filtration on Sephadex G-25 with water yielded 0.95 g (96%) of the pure product. $^1$H NMR (DMSO-d$_6$) δ [ppm]: 11.0 (1H, s), 8.61 (1H, d, J=2.3 Hz), 8.31 (1H, dd, J$_1$=8.4 Hz, J$_2$=2.3 Hz), 8.05 (1H, s), 8.03 (1H, d, J=2.2 Hz), 7.96 (1H, d, J=8.3 Hz), 7.78 (1H, dd, J$_1$=8.4 Hz, J$_2$=2.2 Hz), 7.61 (1H, d, J=8.7 Hz).

B. N,N'-Bis(4-amino-2-sulfobenzoyl)-4,4'-diaminostilbene-2,2-disulfonic Acid Tetrasodium Salt To a sodium hydrogen sulfide solution the product from Part A (0.90 g) was added and the solution was refluxed for 45 minutes. Hydrochloric acid was added to the solution until the pH reached 6, and then the solvent was evaporated under reduced pressure. Water (200 mL) was added, and the resulting precipitate was collected by filtration and washed with water to give 0.45 g (53%) of the title compound. $^1$H NMR (DMSO-d$_6$) δ [ppm]: 11.7 91H, s), 8.00 (1H, s), 7.93 (1H, d, J=2.2 Hz), 7.80 (1H, dd, J$_1$=8.6 Hz, J$_2$=2.1 Hz), 7.58 (1H, d, J=8.4 Hz), 7.54 (1H, d, J=8.8 Hz), 7.18 (1H, d, J=2.3 Hz), 6.55 (1H, dd, J$_1$=8.4 Hz, J$_2$=2.3 Hz), 5.72 (2H, broad).

C. Coupling

The product from Part B, (240 mg, 0.17 mmol) and sodium nitrite (23 mg. 0.33 mmol) were dissolved in water (50 mL). The solution was then poured into a mixture of ice and concentrated hydrochloric acid (0.1 mL, 0.1 g, 0.33 mmol) and stirred for 30 minutes. A second solution was made from 8-hydroxyquinoline-5-sulfonic acid monohydrate (81 mg, 0.33 mmol) and sodium carbonate (38 mg, 0.33 mmol) in water (20 mL). While cooled in an ice bath, the two solutions were mixed and stirred for an hour. The mixture was adjusted to pH 8 by the addition of a small amount of sodium hydroxide solution. The coupling product (240 mg, 62%) was separated by salting out with sodium acetate. $^1$H NMR (DMSO-d$_6$) δ [ppm]: 11.6 (1H, s), 8.90 (1H, d, J=8.2 Hz), 8.54 (1H, d, J=2.2 Hz), 8.33 (1H, s), 8.25 (1H, s, J=small), 8.05 (1H, s), 8.03 (1H, d, J=small), 7.86 (1h, d, J=8.3 Hz), 7.84 (1H, dd, J$_1$=7.7 Hz, J$_2$=small), 7.76 (1H, d, J=7.7 Hz), 7.60 (1H, dd, J$_1$=8.1 Hz, J$_2$=small), 7.44 (1H, dd, J$_1$=8.2 Hz, J$_2$=4.3 Hz). The compound's substituents and their position of attachment are shown in Table 1.

Examples 33–34

Following the procedure set forth in Example 32 and coupling the appropriate diazonium salt derived from the appropriate aniline (II) with 8-hydroxyquinoline-5-sulfonic acid, Compounds 33–34 are obtained.

Example 35

The aroylaniline compounds of the present invention were subjected to in vitro screening to determine their anti-HIV activity.

The National Cancer Institute's procedure for testing for agents active against Human Immunodeficiency Virus (HIV) (Weislow, O. W. et al., "New soluble-formazan assay for HIV-1 cytopathic effects: application to high-flux screening of synthetic and natural products for AIDS-antiviral activity," *J. Natl Cancer Inst.*, 81, 577–586 (1989)) is designed to detect agents acting at any stage of the virus reproductive cycle. The assay includes the killing of T4 lymphocytes by HIV. Pursuant to the test, small amounts of HIV are added to cells, and a complete cycle of virus reproduction is necessary to obtain the required cell killing. Agents that interact with virions, cells, or virus gene-products to interfere with viral activities will protect cells from cytolysis. The system is thus designed to detect anti-HIV activity. However, compounds that are chemically labile or are rapidly metabolized in the culture conditions may not show activity in this screen. All tests are compared with at least one positive (e.g., AZT-treated) control done at the same time under identical conditions.

The Procedure:

1. Candidate agent is dissolved in dimethyl sulfoxide (unless otherwise instructed) and then diluted 1:100 in cell culture medium before preparing serial half-log$_{10}$ dilutions which are then to 96-well microfilter plates. T4 lymphocytes (CEM cell line) are added, and after a brief interval HIV-1 is added to all wells, resulting in a 1:200 final dilution of the compound. Uninfected cells with the compound serve as a toxicity control, and infected and uninfected cells without the compound serve as basic controls.

2. Cultures are incubated at 37° C. in a 5% carbon dioxide atmosphere for 6 days.

3. The tetrazolium salt, XTT, is added to all wells, and cultures are incubated to allow formazan color development by viable cells.

4. Individual wells are analyzed spectrophotometrically to quantitate formazan production, and in addition are viewed microscopically for detection of viable cells and confirmation of protective activity.

5. Drug-tested virus-infected cells are compared with drug-treated noninfected cells and with other appropriate controls (untreated infected and untreated noninfected cells, drug-containing wells without cells, etc.) on the same plate.

6. Data are reviewed in comparison with other tests done at the same time and a determination about activity is made.

The aroylaniline compounds of the present invention were tested for anti-HIV activity according to the above procedure. FIGS. 1–6 represent test results of the aroylaniline compounds of Compounds 1, 3, 13, 14, 29 and 32.

FIGS. 1 to 6 display a plot of the $\log_{10}$ of the concentrations (as μg/mL or molar as shown) of the aroylaniline compounds, Compounds 1, 3, 13, 14, 29 and 32, against the measured test values expressed as a percentage of the uninfected, untreated control values. The solid line depicts the percentage of surviving HIV-infected cells treated with sample (at the indicated concentration) relative to uninfected, untreated controls. Thus, the solid line expresses the anti-HIV activity of the compound. The dashed line depicts the percentage of surviving uninfected cells treated with the compound relative to the same uninfected, untreated controls. Thus, the dashed line expresses the growth inhibitory properties of the compound. The viral cytopathic effect of the compound is indicated by a dotted reference line. The dotted reference line shows the extent of destruction of cells by the virus in the absence of treatment and is used as a quality control parameter. Survival values of this parameter less than 50% are considered acceptable in the current protocol. Approximate values for 50% effective concentration ($EC_{50}$) have been calculated for each test and are set forth for these Compounds in Tables 2–7, respectively.

Table 2 represents the in vitro anti-HIV data for the graph shown in FIG. 1.

TABLE 2

| Summary | | | Percent of | Percent of Control | |
|---|---|---|---|---|---|
| Index | Concentration | Dose (Molar) | Protection | Infected | Un-infected |
| IC50 (Molar) | $1.20 \times 10^{-4}$ | $6.35 \times 10^{-8}$ | −5.09 | 20.13 | 97.61 |
| EC50 (Molar) | $1.44 \times 10^{-6}$ | $2.00 \times 10^{-7}$ | 5.09 | 27.87 | 102.04 |
| TI50 (IC/EC) | $8.28 \times 10^{+1}$ | $6.34 \times 10^{-7}$ | 3.41 | 26.59 | 105.10 |
| Conclusion | | $2.00 \times 10^{-6}$ | 68.63 | 76.16 | 106.46 |
| CONFIRMED ACTIVE | | $6.33 \times 10^{-6}$ | 121.16 | 116.08 | 117.18 |
| | | $2.00 \times 10^{-5}$ | 107.11 | 105.40 | 108.84 |
| | | $6.32 \times 10^{-5}$ | 85.61 | 89.06 | 104.08 |
| | | $2.00 \times 10^{-4}$ | −25.97 | 4.26 | 6.47 |

Figure 2:
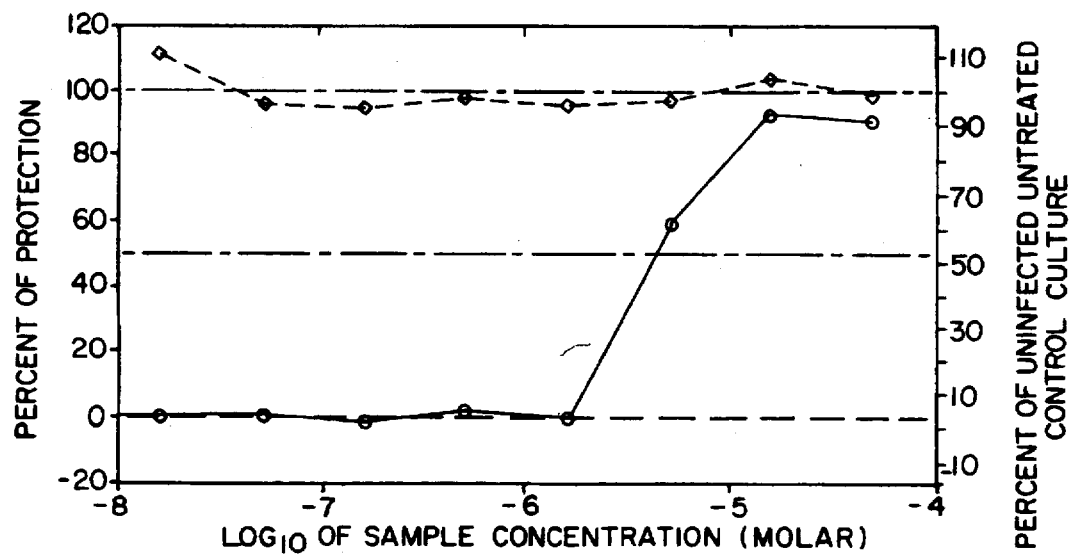
FIG. 2 depicts in vitro testing results for anti-HIV activity for the present inventive compound of Example 3.

Table 3 represents the in vitro anti-HIV data for the graph shown in FIG. 2.

TABLE 3

| Summary | | | Percent of | Percent of Control | |
|---|---|---|---|---|---|
| Index | Concentration | Dose (Molar) | Protection | Infected | Un-infected |
| IC50 (Molar) | $>5.00 \times 10^{-5}$ | $1.58 \times 10^{-8}$ | 0.19 | 4.18 | 110.80 |
| EC50 (Molar) | $4.06 \times 10^{-6}$ | $5.02 \times 10^{-8}$ | 0.51 | 4.49 | 95.85 |
| TI50 (IC/EC) | $>1.23 \times 10^{+1}$ | $1.58 \times 10^{-7}$ | −1.29 | 2.76 | 94.42 |
| Conclusion | | $5.01 \times 10^{-7}$ | 2.00 | 5.92 | 97.72 |
| CONFIRMED ACTIVE | | $1.58 \times 10^{-6}$ | 0.19 | 4.18 | 95.67 |
| | | $5.00 \times 10^{-6}$ | 61.15 | 62.70 | 97.00 |
| | | $1.58 \times 10^{-5}$ | 92.90 | 93.18 | 103.32 |
| | | $5.00 \times 10^{-5}$ | 90.76 | 91.13 | 97.98 |

Figure 3:
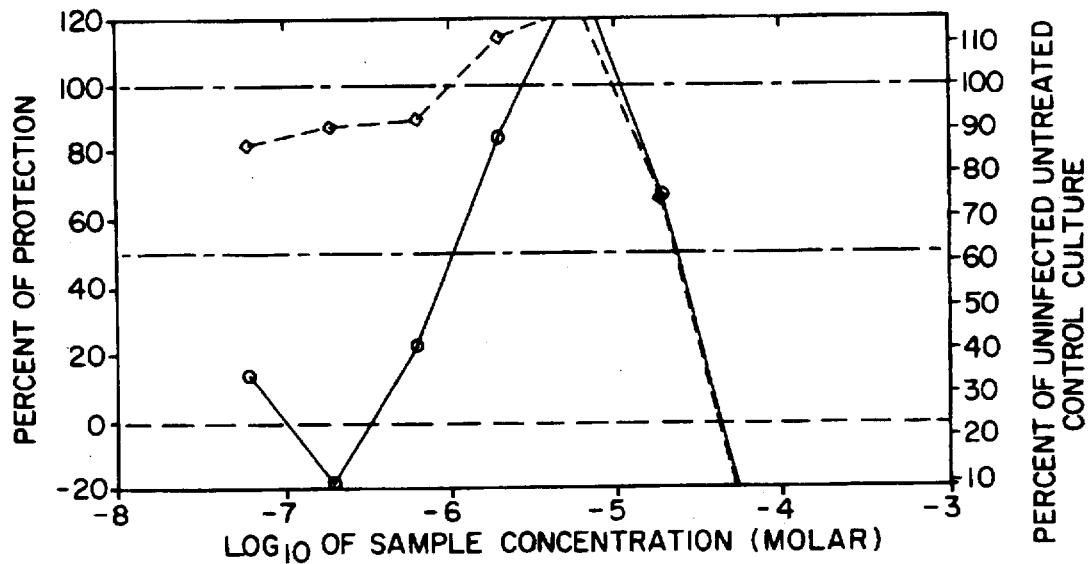
FIG. 3 depicts in vitro testing results for anti-HIV activity for the present inventive compound of Example 13.

Table 4 represents the in vitro anti-HIV data for the graph shown in FIG. 3.

TABLE 4

| Summary | | | Percent of | Percent of Control | |
|---|---|---|---|---|---|
| Index | Concentration | Dose (Molar) | Protection | Infected | Un-infected |
| IC50 (Molar) | $2.90 \times 10^{-5}$ | $6.35 \times 10^{-8}$ | 15.57 | 35.83 | 86.36 |
| EC50 (Molar) | $1.05 \times 10^{-6}$ | $2.00 \times 10^{-7}$ | −17.92 | 10.38 | 90.55 |
| TI50 (IC/EC) | $2.78 \times 10^{+1}$ | $6.34 \times 10^{-7}$ | 24.57 | 42.67 | 92.22 |
| Conclusion | | $2.00 \times 10^{-6}$ | 84.38 | 88.13 | 110.93 |
| CONFIRMED ACTIVE | | $6.33 \times 10^{-6}$ | 133.79 | 125.68 | 117.81 |
| | | $2.00 \times 10^{-5}$ | 67.54 | 75.33 | 73.70 |
| | | $6.32 \times 10^{-5}$ | 29.43 | 1.63 | 0.37 |
| | | $2.00 \times 10^{-4}$ | −28.03 | 2.70 | 2.05 |

Figure 4:
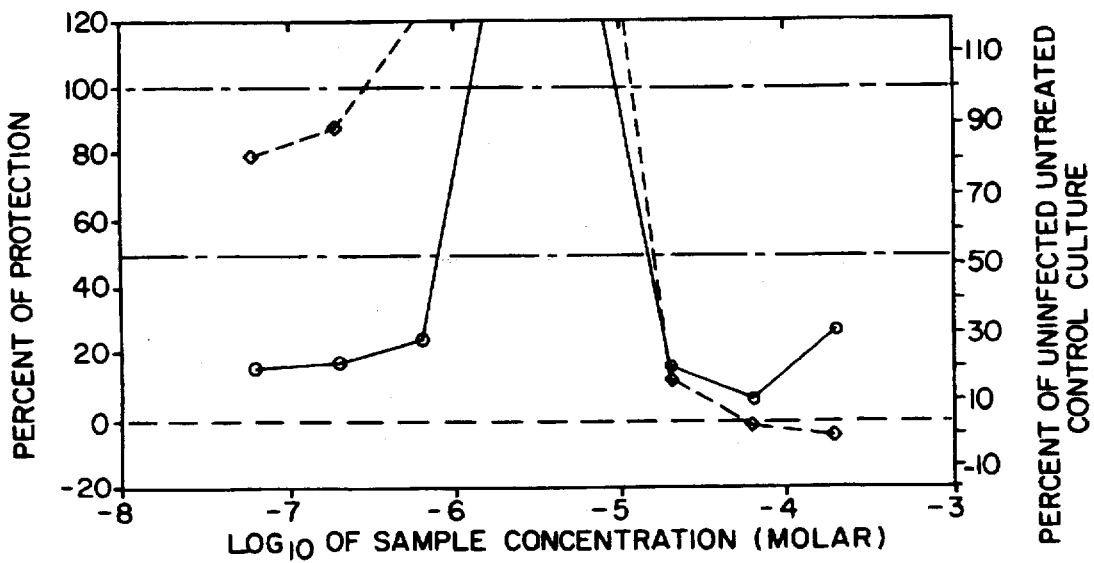
FIGS. 4 depicts in vitro testing results for anti-HIV activity for the present inventive compound of Example 14.

Table 5 represents the in vitro anti-HIV data for the graph shown in FIG. 4.

TABLE 5

| Summary | | | Percent of | Percent of Control | |
|---|---|---|---|---|---|
| Index | Concentration | Dose (Molar) | Protection | Infected | Un-infected |
| IC50 (Molar) | $1.65 \times 10^{-5}$ | $6.35 \times 10^{-8}$ | 16.02 | 18.54 | 80.16 |
| EC50 (Molar) | $8.05 \times 10^{-7}$ | $2.00 \times 10^{-7}$ | 17.57 | 20.04 | 88.92 |
| TI50 (IC/EC) | $2.05 \times 10^{+2}$ | $6.34 \times 10^{-7}$ | 24.99 | 27.24 | 121.68 |
| Conclusion | | $2.00 \times 10^{-6}$ | 146.91 | 145.50 | 205.56 |
| CONFIRMED ACTIVE | | $6.33 \times 10^{-6}$ | 150.93 | 149.40 | 220.68 |
| | | $2.00 \times 10^{-5}$ | 16.58 | 19.08 | 15.48 |
| | | $6.32 \times 10^{-5}$ | 6.56 | 9.36 | 2.52 |
| | | $2.00 \times 10^{-4}$ | 27.65 | 29.82 | −0.84 |

Figure 5:
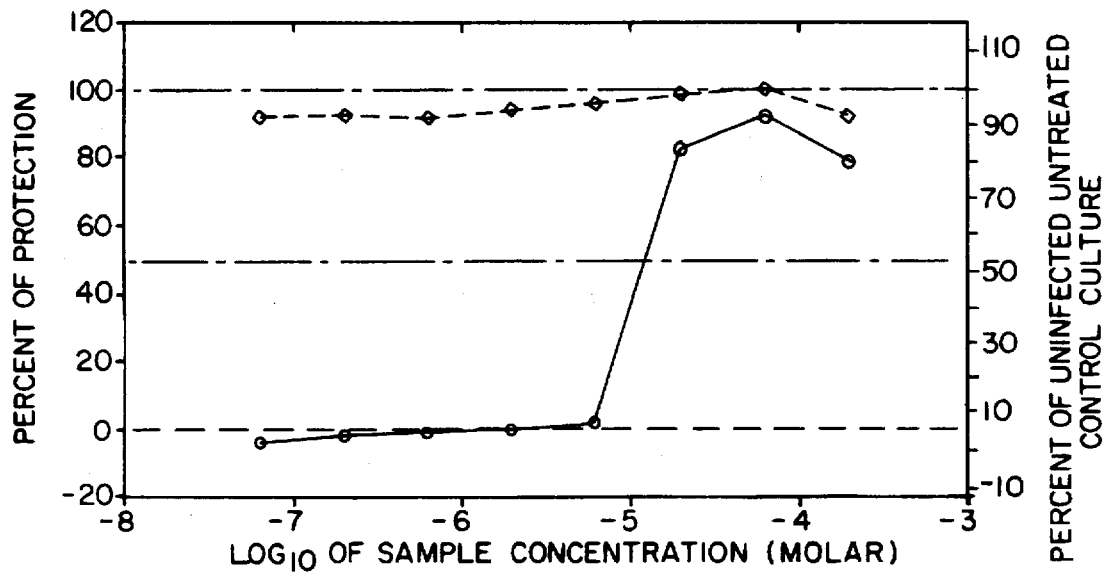
FIG. 5 depicts in vitro testing results for anti-HIV activity for the present inventive compound of Example 29.

Table 6 represents the in vitro anti-HIV data for the graph shown in FIG. 5.

TABLE 6

| Summary | | | Percent of | Percent of Control | |
|---|---|---|---|---|---|
| Index | Concentration | Dose (Molar) | Protection | Infected | Un-infected |
| IC50 (Molar) | $>2.20 \times 10^{-4}$ | $6.35 \times 10^{-8}$ | −3.31 | 3.92 | 93.21 |
| EC50 (Molar) | $1.25 \times 10^{-5}$ | $2.00 \times 10^{-7}$ | −1.09 | 5.99 | 93.77 |
| TI50 (IC/EC) | $>1.61 \times 10^{+1}$ | $6.34 \times 10^{-7}$ | −0.52 | 6.52 | 92.80 |
| Conclusion | | $2.00 \times 10^{-6}$ | 0.58 | 7.54 | 95.15 |
| CONFIRMED ACTIVE | | $6.33 \times 10^{-6}$ | 2.47 | 9.30 | 96.67 |
| | | $2.00 \times 10^{-5}$ | 83.30 | 84.47 | 99.02 |
| | | $6.32 \times 10^{-5}$ | 92.72 | 93.23 | 100.14 |
| | | $2.00 \times 10^{-4}$ | 79.66 | 81.08 | 92.95 |

Figure 6:
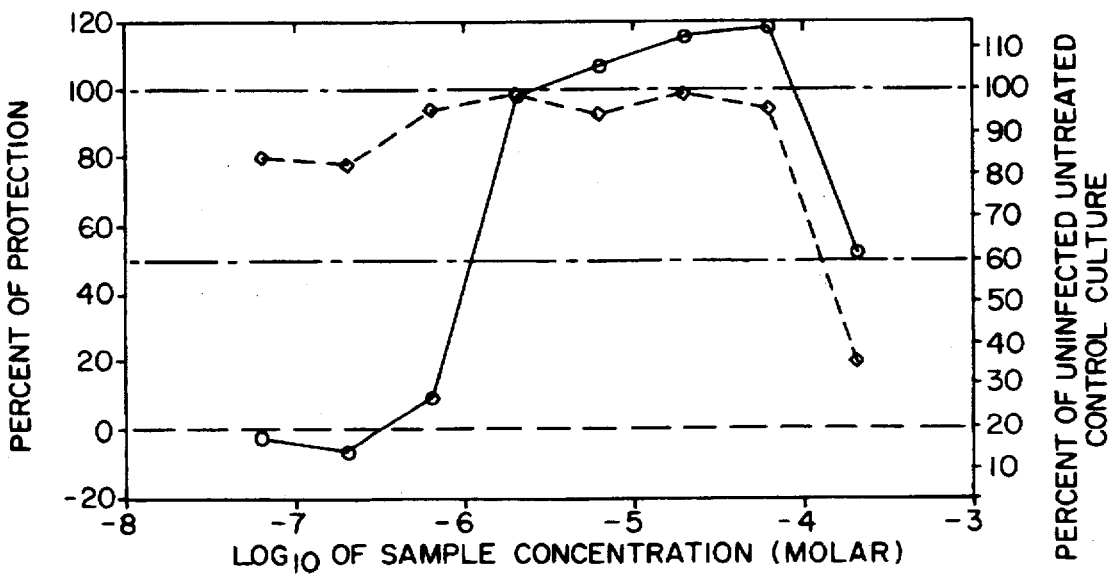
FIG. 6 depicts in vitro testing results for anti-HIV activity for the present inventive compound of Example 32.

Table 7 represents the in vitro anti-HIV data for the graph shown in FIG. 6.

TABLE 7

| Summary | | | Percent of | Percent of Control | |
|---|---|---|---|---|---|
| Index | Concentration | Dose (Molar) | Protection | Infected | Un-infected |
| IC50 (Molar) | $1.51 \times 10^{-4}$ | $6.36 \times 10^{-8}$ | −2.32 | 17.12 | 83.94 |
| EC50 (Molar) | $1.08 \times 10^{-6}$ | $2.01 \times 10^{-7}$ | −6.05 | 14.10 | 82.40 |
| TI50 (IC/EC) | $1.40 \times 10^{+2}$ | $6.35 \times 10^{-7}$ | 9.69 | 26.85 | 95.11 |
| Conclusion | | $2.01 \times 10^{-6}$ | 97.49 | 97.97 | 98.97 |
| CONFIRMED ACTIVE | | $6.34 \times 10^{-6}$ | 106.98 | 105.65 | 94.34 |
| | | $2.00 \times 10^{-5}$ | 115.65 | 112.68 | 98.84 |

TABLE 7-continued

| Index | Summary Concentration | Dose (Molar) | Percent of Protection | Percent of Control Infected | Un-infected |
|---|---|---|---|---|---|
| | | 6.33 × 10⁻⁵ | 118.99 | 115.38 | 95.50 |
| | | 2.00 × 10⁻⁴ | 52.90 | 61.85 | 35.45 |

As illustrated in FIGS. 1–6 and Tables 2–7, the aroylaniline compounds of the present invention are effective in protecting cells from cytolysis. Their therapeutic index, $TI_{50}$ (IC/EC) is indicated on their graphs and in their respective tables.

All references cited herein are incorporated in their entireties by reference.

While this invention has been described with emphasis upon preferred embodiments, it will be obvious to those skilled in the art that variations in the preferred compounds and methods may be used and that it is intended that the invention may be practiced otherwise then as specifically described herein. Accordingly, this invention includes all modifications encompassed within the spirit and scope of the invention as defined by the following claims.

What is claimed is:

1. An aroylaniline compound having the formula:

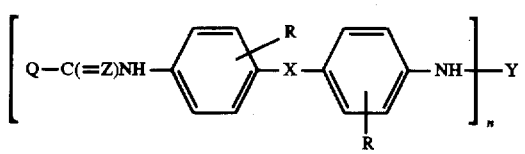
(I)

wherein R is —H, —SO₃.E, —CO₂.E, —PO(O)₂2.E, —NO₂, or a halogen;

Q is

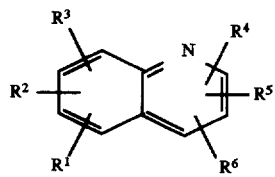

Y is

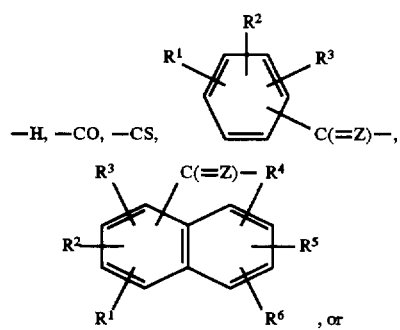

—H, —CO, —CS,

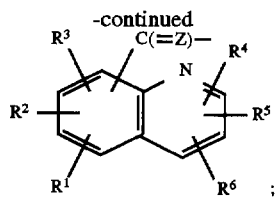

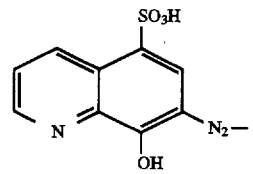

$R^1$, $R^2$, $R^3$, $R^4$, $R^5$ and $R^6$ are each independently —H, —OH, a halogen, —NH₂, —NHCH₃, —N(CH₃)₂, —CHO, CH₃O—, —SO₃.E, —NO₂, —CO₂.E, —PO(O)₂2.E, —CH₂OH, —CH₂SCH₂COR⁷, —CH₂S—C₂H₄COR⁷, —CH₂S—CH(CO₂H)CH₂COR⁷, —CH₂S—CH(CO₂H)CH₂CO₂R⁷, —CH₂SCH₂CO₂R⁷, —CH₂SC₂H₄CO₂R⁷ or

[Structure: quinoline with SO₃H, OH, N₂— substituents]

wherein E represents H, lithium, sodium, potassium, ammonium, magnesium, (HOC₂H₄)₃NH, (CH₃)₃NH, CH₃NH(C₂H₄OH)₂, (CH₃)₄N—, or HN-methylglucamine and wherein R⁷ is H, methyl, ethyl, benzyl, —NH₂, —NHCH₃, or —NHC₂H₅;

X is —CH=CH—, —CH₂CH₂—, —CONH—, —NHCONH—, —NHCSNH—, —S—, —SO—, —SO₂—, —NH—, —CH₂— or cyclopropyl;

Z is oxygen or sulfur; and n is 1 or 2, but when n is 1, Y is H,

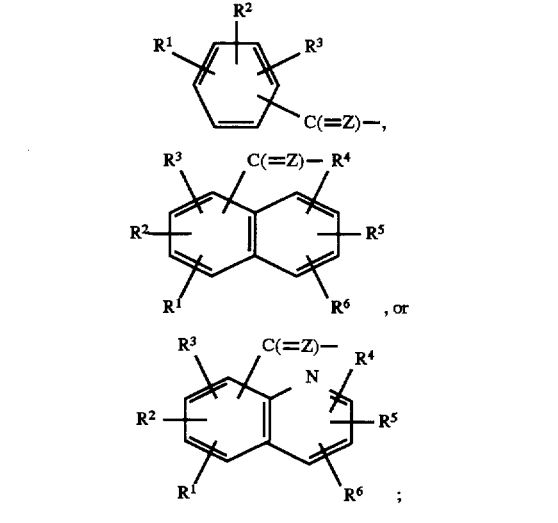

and when n is 2, Y is —CO or —CS.

2. The aroylaniline compound of claim 1 wherein the compound has the formula:

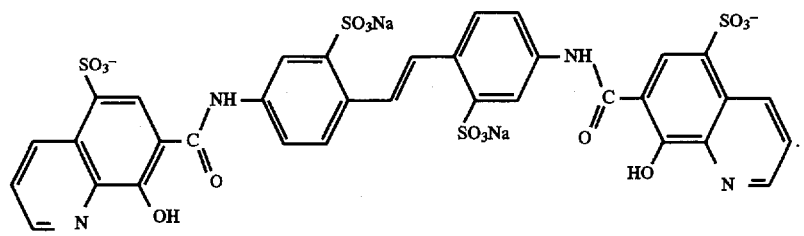
3. The aroylaniline compound of claim 1 wherein the compound has the formula:
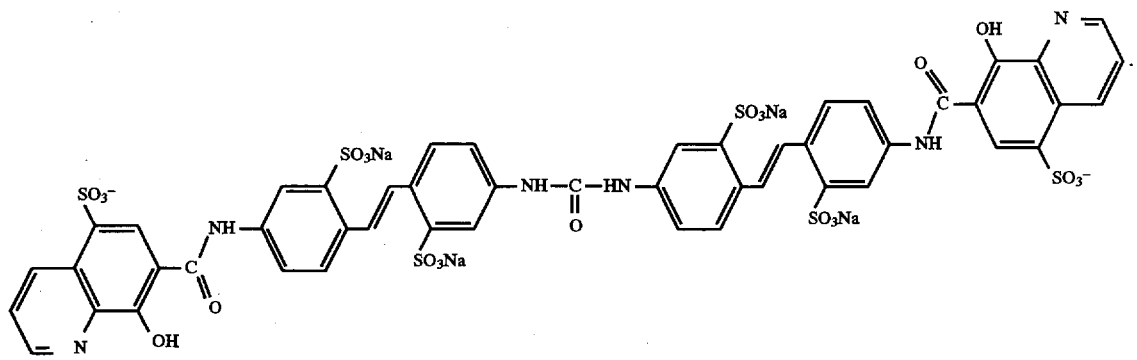
4. The aroylaniline compound of claim 1 wherein the compound has the formula:
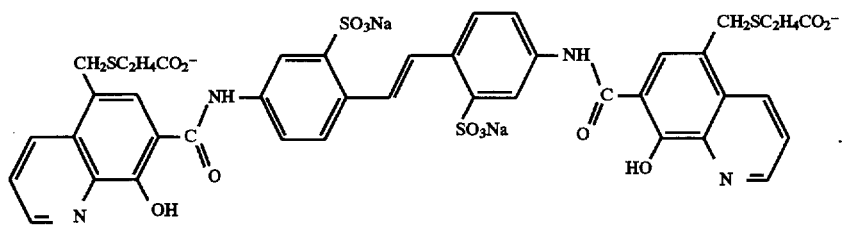
5. The aroylaniline compound of claim 1 wherein the compound has the formula:
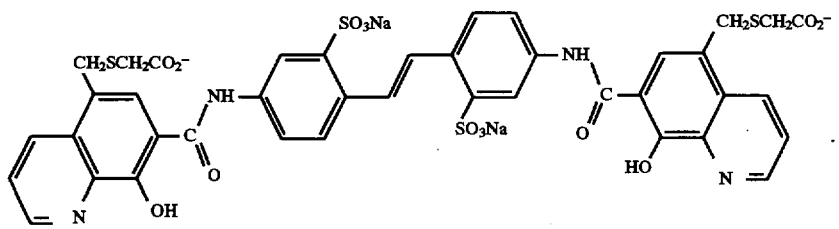
6. The aroylaniline compound of claim 1 wherein the compound has the formula:

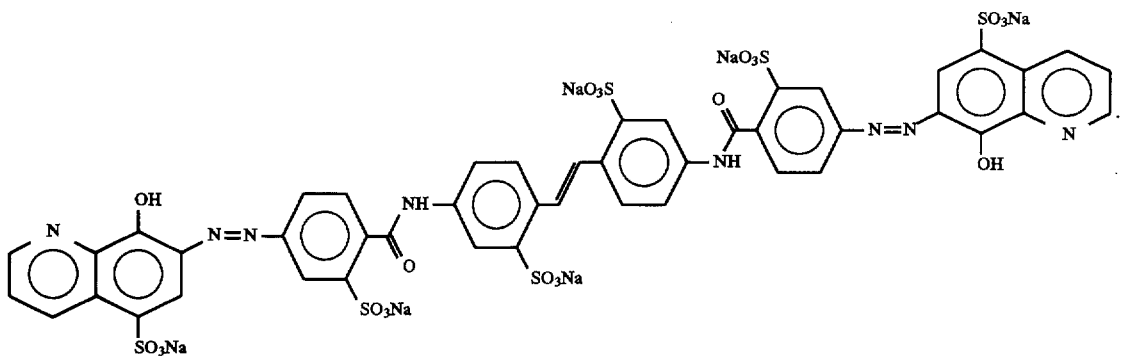

7. A pharmaceutical composition comprising the aroylaniline compound of claim 2 and a pharmaceutically acceptable carrier.

8. A pharmaceutical composition comprising the aroylaniline compound of claim 3 and a pharmaceutically acceptable carrier.

9. A pharmaceutical composition comprising the aroylaniline compound of claim 4 and a pharmaceutically acceptable carrier.

10. A pharmaceutical composition comprising the aroylaniline compound of claim 5 and a pharmaceutically acceptable carrier.

11. A pharmaceutical composition comprising the aroylaniline compound of claim 6 and a pharmaceutically acceptable carrier.

12. The aroylaniline derivative of claim 1, wherein Y is selected from the group consisting of:

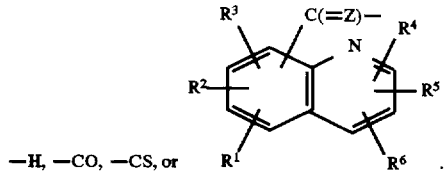

13. A pharmaceutical composition comprising a pharmaceutically acceptable carrier and an aroylaniline compound having the structural formula:

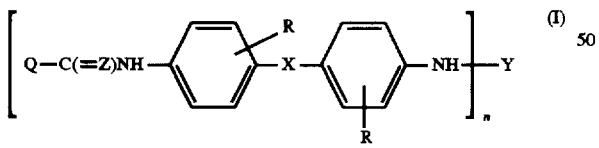

wherein R is —H, —SO$_3$.E, —CO$_2$.E, —PO(O)$_2$.2E, —NO$_2$, or a halogen;

Q is

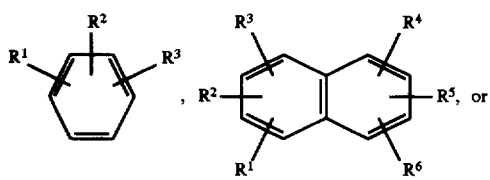

-continued

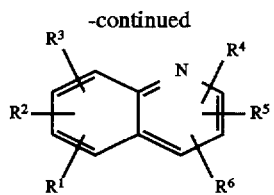

Y is

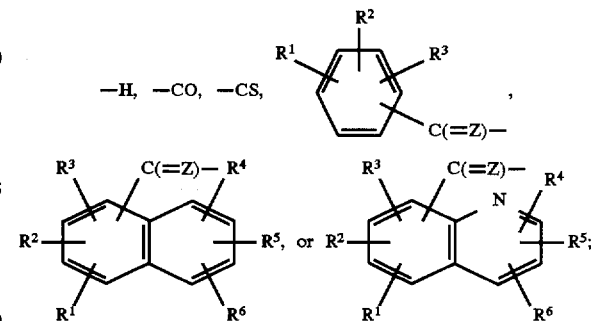

$R^1$, $R^2$, $R^3$, $R^4$, $R^5$ and $R^6$ are each independently —H, —OH, a halogen, —NH$_2$, —NHCH$_3$, —N(CH$_3$)$_2$, —CHO, CH$_3$O—, —SO$_3$.E, —NO$_2$, —CO$_2$.E, —PO(O)$_2$.2E, —CH$_2$OH, —CH$_2$SCH$_2$COR$^7$, —CH$_2$S—C$_2$H$_4$COR$^7$, —CH$_2$S—CH(CO$_2$H)CH$_2$COR$^7$, —CH$_2$S—CH(CO$_2$H)CH$_2$CO$_2$R$^7$, —CH$_2$SCH$_2$CO$_2$R$^7$, —CH$_2$SC$_2$H$_4$CO$_2$R$^7$ or

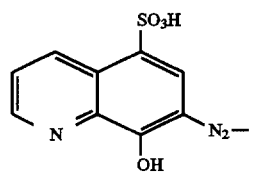

wherein E represents H, lithium, sodium, potassium, ammonium, magnesium, (HOC$_2$H$_4$)$_3$NH, (CH$_3$)$_3$NH, CH$_3$NH(C$_2$H$_4$OH)$_2$, (CH$_3$)$_4$N—, or HN-methylglucamine and wherein R$^7$ is H, methyl, ethyl, benzyl, —NH$_2$, —NHCH$_3$, or —NHC$_2$H$_5$;

X is —CH=CH—, —CH$_2$CH$_2$—, —CONH—, —NHCONH—, —NHCSNH—, —S—, —SO—, —SO$_2$—, —NH—, —CH$_2$— or cyclopropyl;

Z is oxygen or sulfur; and n is 1 or 2, but when n is 1, Y is H,

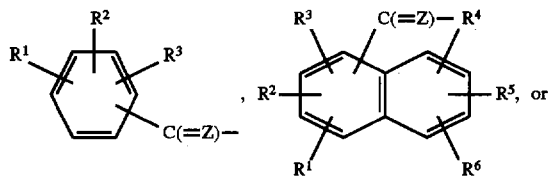

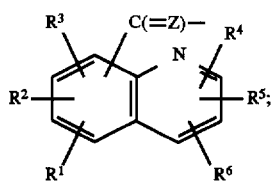

and when n is 2, Y is —CO or —CS.

14. A method for treating a viral infection of a host which comprises administering to said host an antiviral effective amount of an aroylaniline compound having the structural formula:

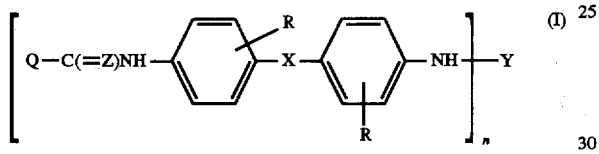

wherein R is —H, —SO$_3$.E, —CO$_2$.E, —PO(O)$_2$.2E, —NO$_2$, or a halogen;

Q is

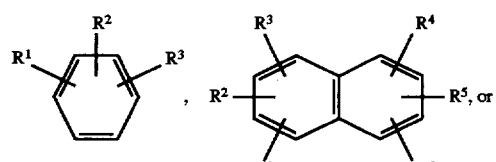

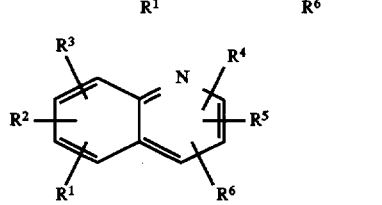

Y is

—H, —CO, —CS,

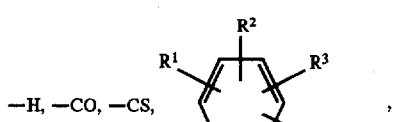

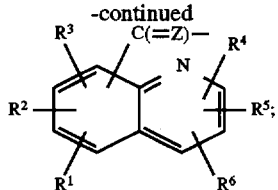

-continued

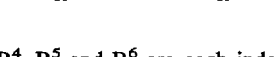

$R^1$, $R^2$, $R^3$, $R^4$, $R^5$ and $R^6$ are each independently —H, —OH, a halogen, —NH$_2$, —NHCH$_3$, —N(CH$_3$)$_2$, —CHO, CH$_3$O—, —SO$_3$.E, —NO$_2$, —CO$_2$.E, —PO(O)$_2$.2E, —CH$_2$OH, —CH$_2$SCH$_2$COR$^7$, —CH$_2$S—C$_2$H$_4$COR$^7$, —CH$_2$S—CH(CO$_2$H)CH$_2$COR$^7$, —CH$_2$S—CH(CO$_2$H)CH$_2$CO$_2$R$^7$, —CH$_2$SCH$_2$CO$_2$R$^7$, —CH$_2$SC$_2$H$_4$CO$_2$R$^7$ or

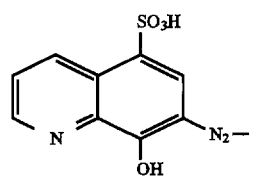

wherein E represents H, lithium, sodium, potassium, ammonium, magnesium, (HOC$_2$H$_4$)$_3$NH, (CH$_3$)$_3$NH, CH$_3$NH(C$_2$H$_4$OH)$_2$, (CH$_3$)$_4$N—, or HN-methylglucamine and wherein R$^7$ is H, methyl, ethyl, benzyl, —NH$_2$, —NHCH$_3$, or —NHC$_2$H$_5$;

X is —CH=CH—, —CH$_2$CH$_2$—, —CONH—, —NHCONH—, —NHCSNH—, —S—, —SO—, —SO$_2$—, —NH—, —CH$_2$— or cyclopropyl;

Z is oxygen or sulfur; and n is 1 or 2, but when n is 1, Y is H,

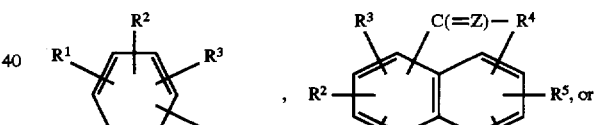

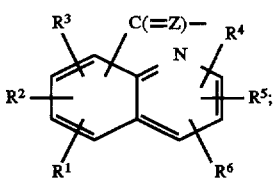

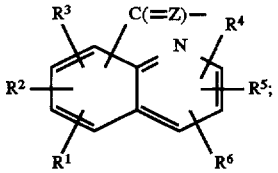

and when n is 2, Y is —CO or —CS.

15. A method for inhibiting replication of a retrovirus comprising contacting said retrovirus with a retrovirally effective amount of an aroylaniline compound having the structural formula:

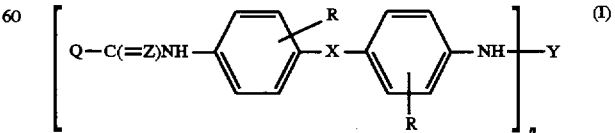

wherein R is —H, —SO$_3$.E, —CO$_2$.E, —PO(O)$_2$.2E, —NO$_2$, or a halogen;

Q is

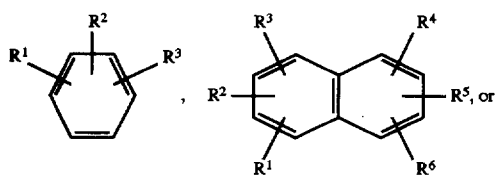

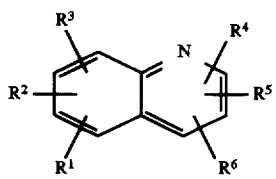

Y is

—H, —CO, —CS,

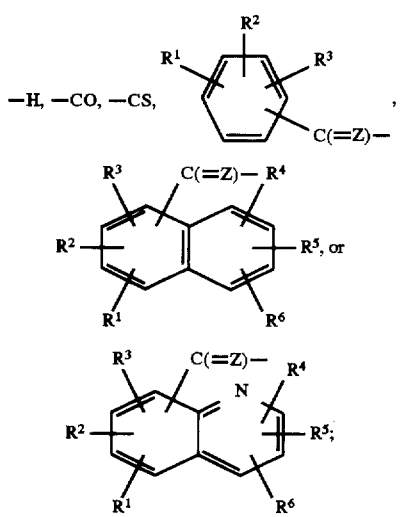

$R^1$, $R^2$, $R^3$, $R^4$, $R^5$ and $R^6$ are each independently —H, —OH, a halogen, —NH$_2$, —NHCH$_3$, —N(CH$_3$)$_2$, —CHO, CH$_3$O—, —SO$_3$.E, —NO$_2$, —CO$_2$.E, —PO(O)$_2$.2E, —CH$_2$OH, —CH$_3$SCH$_2$COR$^7$, —CH$_2$S—C$_2$H$_4$COR$^7$, —CH$_2$S—CH(CO$_2$H)CH$_2$COR$^7$, —CH$_2$S—CH(CO$_2$H)CH$_2$CO$_2$R$^7$, —CH$_2$SCH$_2$CO$_2$R$^7$, —CH$_2$SC$_2$H$_4$CO$_2$R$^7$ or

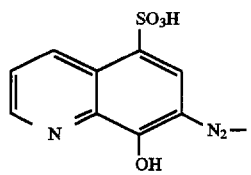

wherein E represents H, lithium, sodium, potassium, ammonium, magnesium, (HOC$_2$H$_4$)$_3$NH, (CH$_3$)$_3$NH, CH$_3$NH(C$_2$H$_4$OH)$_2$, (CH$_3$)$_4$N—, or HN-methylglucamine and wherein R$^7$ is H, methyl, ethyl, benzyl, —NH$_2$, —NHCH$_3$, or —NHC$_2$H$_5$;

X is —CH=CH—, —CH$_2$CH$_2$—, —CONH—, —NHCONH—, —NHCSNH—, —S—, —SO—, —SO$_2$—, —NH—, —CH$_2$— or cyclopropyl;

Z is oxygen or sulfur; and n is 1 or 2, but when n is 1, Y is H,

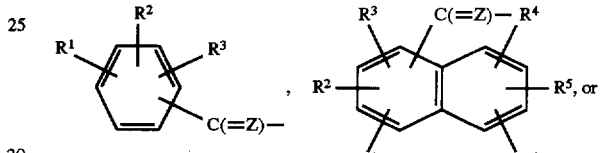

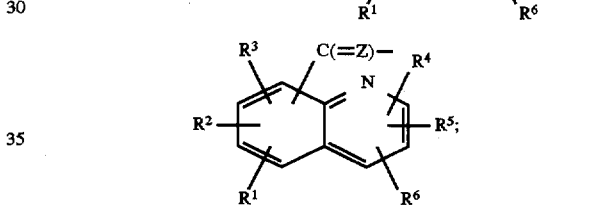

and when n is 2, Y is —CO or —CS.

16. The method of claim 14, wherein the viral infection is an HIV infection.

17. The method of claim 16, wherein the aroylaniline compound is a compound having the formula:

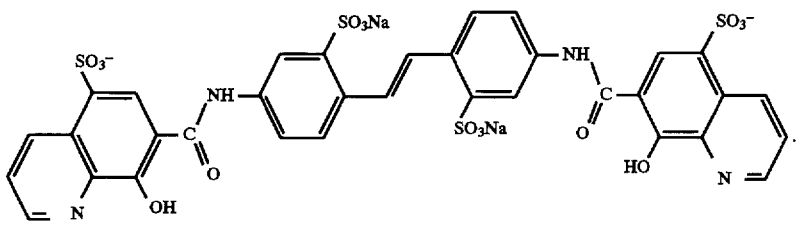

18. The method of claim 16, wherein the aroylaniline compound is a compound having the formula:

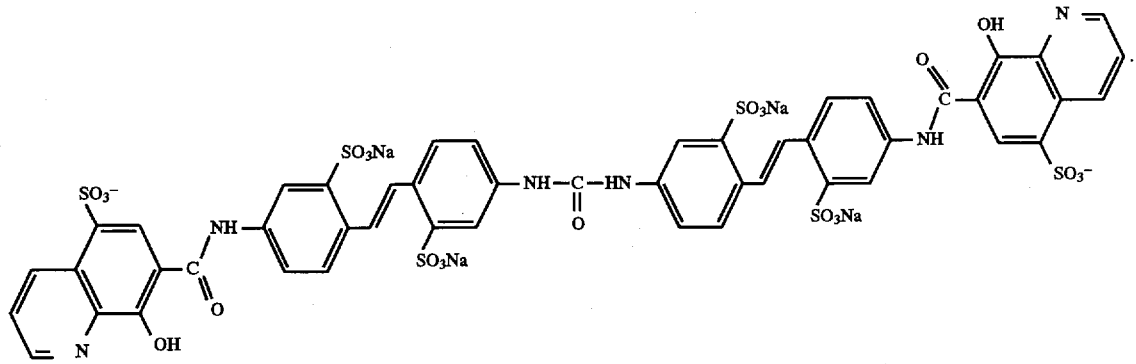

19. The method of claim 16, wherein the aroylaniline compound is a compound having the formula:

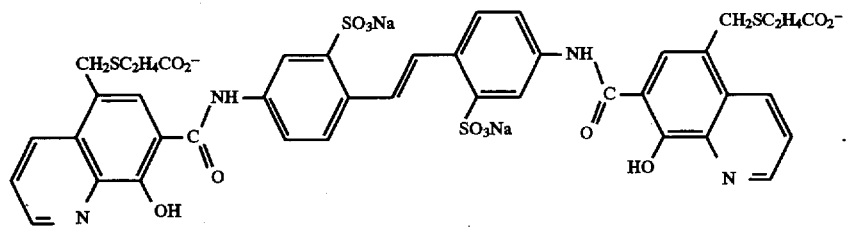

20. The method of claim 16, wherein the aroylaniline compound is a compound having the formula:

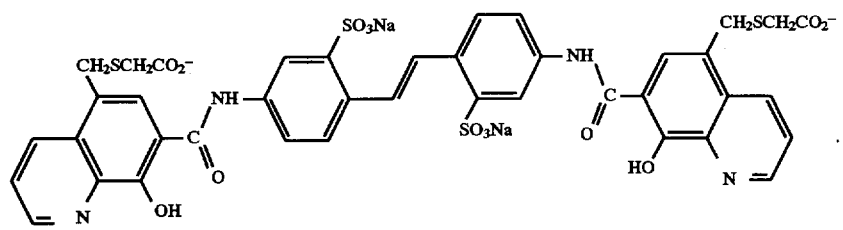

21. The method of claim 16, wherein the aroylaniline compound is a compound having the formula:

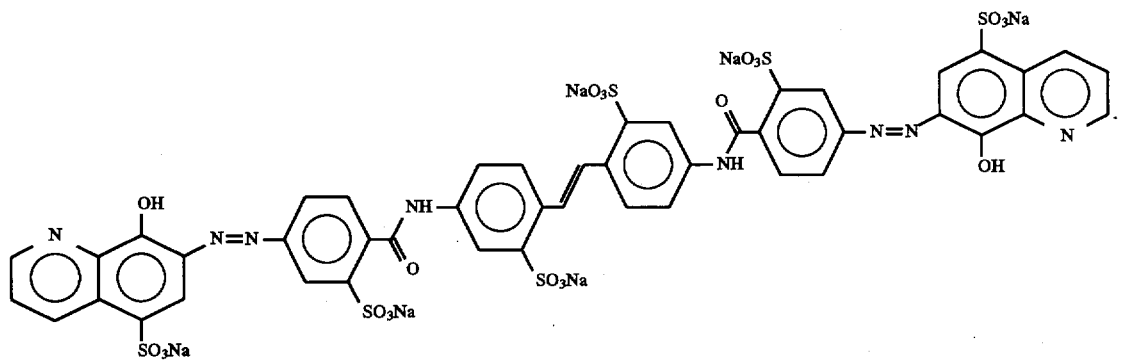

22. The method of claim 15, wherein said retrovirus is a human immunodeficiency virus.

23. A method for treating a retroviral infection in a mammal comprising administering a retrovirally effective amount of an aroylanilline compound having the structural formula:

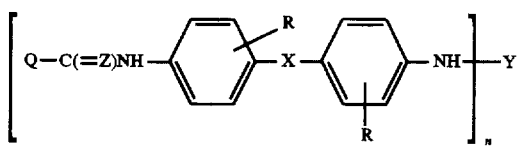

where R is —H, —SO₃.E, —CO₂.E, —PO(O)₂.2E, —NO₂, or a halogen;

Q is

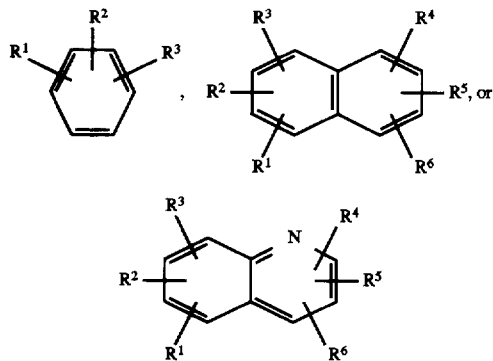

Y is

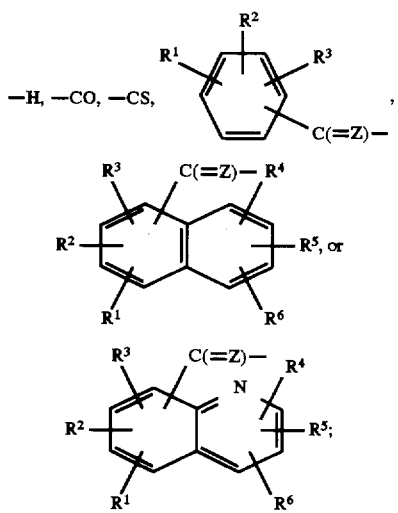

$R^1$, $R^2$, $R^3$, $R^4$, $R^5$ and $R^6$ are each independently —H, —OH, a halogen, —NH₂, —NHCH₃, —N(CH₃)₂, —CHO, CH₃O—, —SO₃.E, —NO₂, —CO₂.E, —PO(O)₂.2E, —CH₂OH, —CH₂SCH₂COR⁷, —CH₂S—C₂H₄COR⁷, —CH₂S—CH(CO₂H)CH₂COR⁷, —CH₂S—CH(CO₂H)CH₂CO₂R⁷, —CH₂SCH₂CO₂R⁷, —CH₂SC₂H₄CO₂R⁷ or

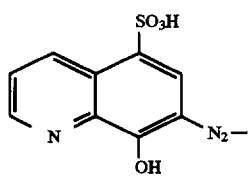

wherein E represents H, lithium, sodium, potassium, ammonium, magnesium, (HOC₂H₄)₃NH, (CH₃)₃NH, CH₃NH(C₂H₄OH)₂, (CH₃)₄N—, or HN-methylglucamine and wherein $R^7$ is H, methyl, ethyl, benzyl, —NH₂, —NHCH₃, or —NHC₂H₅;

X is —CH=CH—, —CH₂CH₂—, —CONH—, —NHCONH—, —NHCSNH—, —S—, —SO—, —SO₂—, —NH—, —CH₂— or cyclopropyl;

Z is oxygen or sulfur; and n is 1 or 2, but when n is 1, Y is H,

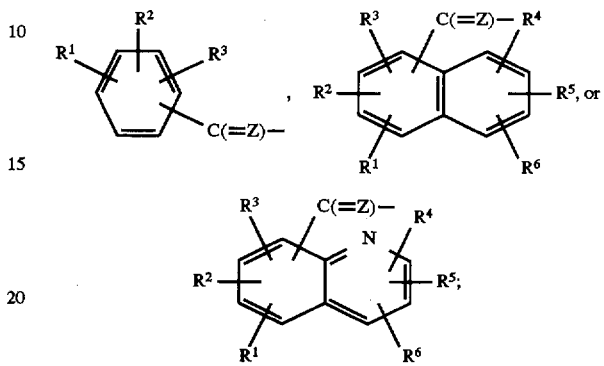

and when n is 2, Y is —CO or —CS.

24. The method of claim 23, wherein said mammal is a human.

25. The method of claim 24, wherein said retroviral infection is an HIV infection.

26. A method for inhibiting replication of a virus in vitro comprising contacting said virus with an anti-virally effective amount of an aroylaniline compound having the structural formula:

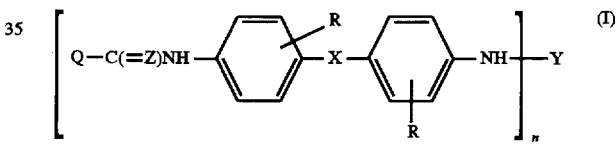

wherein R is —H, —SO₃.E, —CO₂.E, —PO(O)₂.2E, —NO₂, or a halogen;

Q is

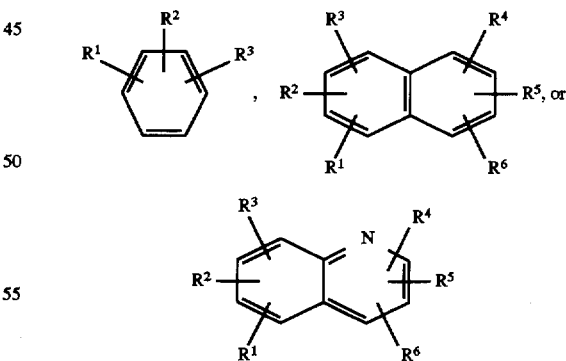

Y is

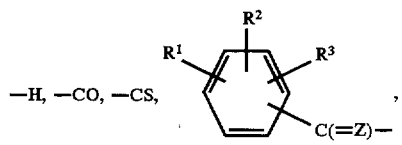

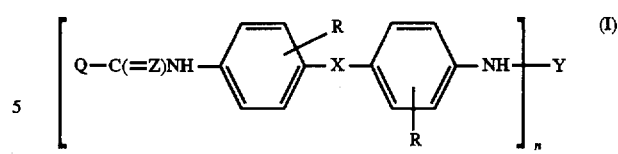

wherein R is —H, —SO₃.E, —CO₂.E, —PO(O)₂.2E, —NO₂, or a halogen;

Q is

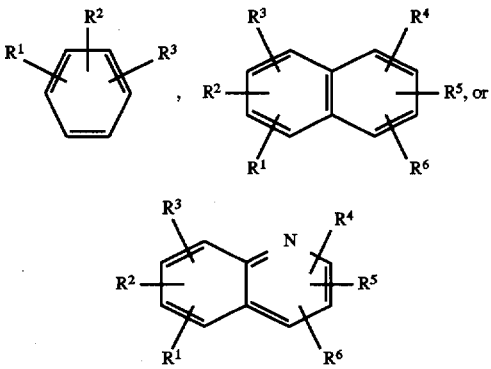

Y is

—H, —CO, —CS,

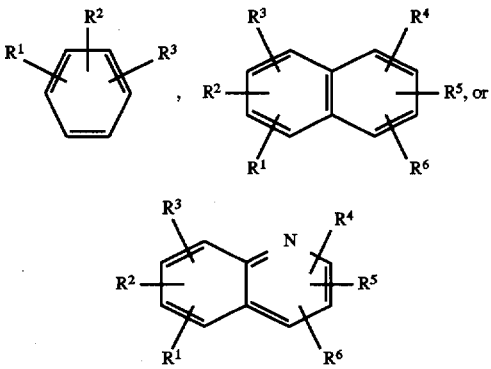

$R^1$, $R^2$, $R^3$, $R^4$, $R^5$ and $R^6$ are each independently —H, —OH, a halogen, —NH₂, —NHCH₃, —N(CH₃)₂, —CHO, CH₃O—, —SO₃.E, —NO₂, —CO₂.E, —PO(O)₂.2E, —CH₂OH, —CH₂SCH₂COR⁷, —CH₂S—C₂H₄COR⁷, —CH₂S—CH(CO₂H)CH₂COR⁷, —CH₂S—CH(CO₂H)CH₂CO₂R⁷, —CH₂SCH₂CO₂R⁷, —CH₂SC₂H₄CO₂R⁷ or

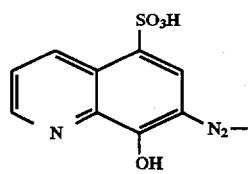

wherein E represents H, lithium, sodium, potassium, ammonium, magnesium, (HOC₂H₄)₃NH, (CH₃)₃NH, CH₃NH(C₂H₄OH)₂, (CH₃)₄N—, or HN-methylglucamine

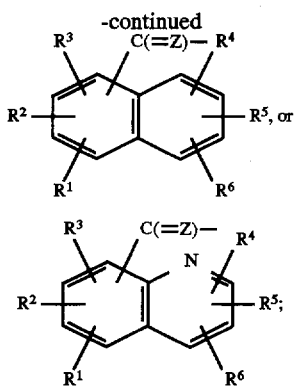

$R^1$, $R^2$, $R^3$, $R^4$, $R^5$ and $R^6$ are each independently —H, —OH, a halogen, —NH₂, —NHCH₃, —N(CH₃)₂, —CHO, CH₃O—, —SO₃.E, —NO₂, —CO₂.E, —PO(O)₂.2E, —CH₂OH, —CH₂SCH₂COR⁷, —CH₂S—C₂H₄COR⁷, —CH₂S—CH(CO₂H)CH₂COR⁷, —CH₂S—CH(CO₂H)CH₂CO₂R⁷, —CH₂SCH₂CO₂R⁷, —CH₂SC₂H₄CO₂R⁷ or

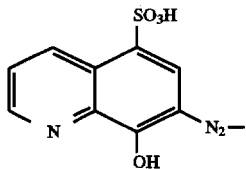

wherein E represents H, lithium, sodium, potassium, ammonium, magnesium, (HOC₂H₄)₃NH, (CH₃)₃NH, CH₃NH(C₂H₄OH)₂, (CH₃)₄N—, or HN-methylglucamine and wherein R⁷ is H, methyl, ethyl, benzyl, —NH₂, —NHCH₃, or —NHC₂H₅;

X is —CH=CH—, —CH₂CH₂—, —CONH—, —NHCONH—, —NHCSNH—, —S—, —SO—, —SO₂—, —NH—, —CH₂— or cyclopropyl;

Z is oxygen or sulfur; and n is 1 or 2, but when n is 1, Y is H,

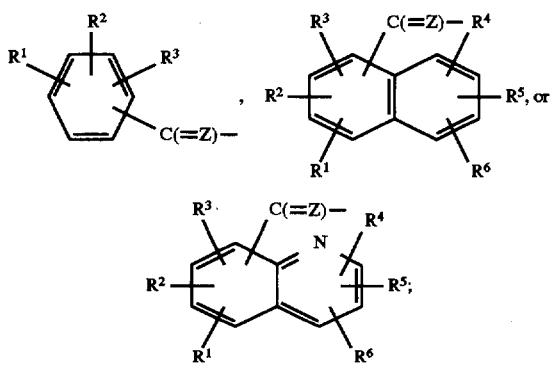

and when n is 2, Y is —CO or —CS.

27. The method of claim 26, wherein said virus is a retrovirus.

28. The method of claim 27, wherein said retrovirus is a human immunodeficiency virus.

29. A method for preventing a mammal from being infected by a herpes virus comprising administering a prophylactively effective amount of an aroylaniline compound having the structural formula:

and wherein $R^7$ is H, methyl, ethyl, benzyl, —$NH_2$, —$NHCH_3$, or —$NHC_2H_5$;
X is —CH=CH—, —$CH_2CH_2$—, —CONH—, —NHCONH—, —NHCSNH—, —S—, —SO—, —$SO_2$—, —NH—, —$CH_2$— or cyclopropyl;
Z is oxygen or sulfur; and
n is 1 or 2, but when n is 1, Y is H,
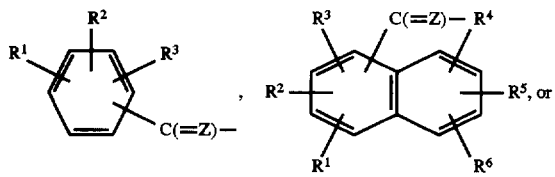
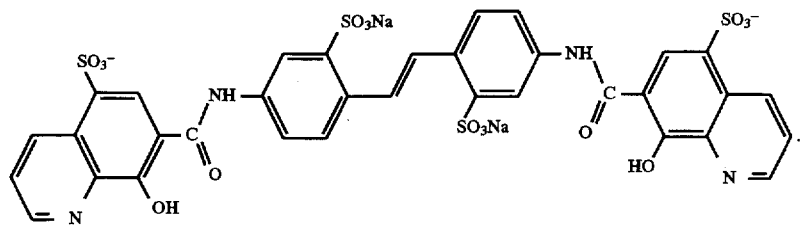
and when n is 2, Y is —CO or —CS.
30. The method of claim 26, wherein said aroylaniline compound has the formula:
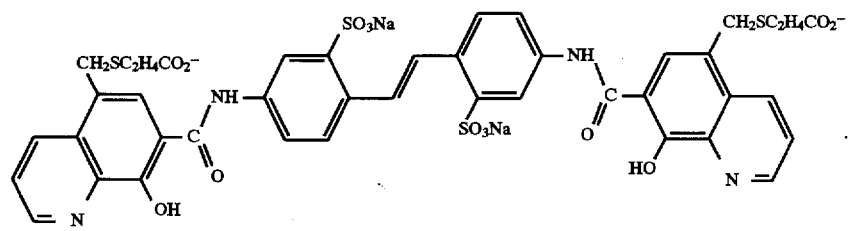
31. The method of claim 26, wherein said aroylaniline compound has the formula:
* * * * *